United States Patent
Fernandez-Gomez

(10) Patent No.: US 11,139,047 B2
(45) Date of Patent: Oct. 5, 2021

(54) ADAPTIVE NANOPORE SIGNAL COMPRESSION

(71) Applicant: Roche Sequencing Solutions, Inc., Pleasanton, CA (US)

(72) Inventor: Santiago Fernandez-Gomez, Sunnyvale, CA (US)

(73) Assignee: Roche Sequencing Solutions, Inc., Pleasanton, CA (US)

(*) Notice: Subject to any disclaimer, the term of this patent is extended or adjusted under 35 U.S.C. 154(b) by 822 days.

(21) Appl. No.: 15/844,244

(22) Filed: Dec. 15, 2017

(65) Prior Publication Data
US 2018/0173844 A1   Jun. 21, 2018

Related U.S. Application Data

(60) Provisional application No. 62/435,033, filed on Dec. 15, 2016.

(51) Int. Cl.
*G01N 33/48*   (2006.01)
*G01N 33/50*   (2006.01)
(Continued)

(52) U.S. Cl.
CPC .......... *G16B 30/00* (2019.02); *C12Q 1/68* (2013.01); *C12Q 1/6869* (2013.01); *G01N 33/48721* (2013.01); *H03M 7/3084* (2013.01)

(58) Field of Classification Search
CPC ........ G16B 30/00; C12Q 1/6869; C12Q 1/68; G01N 33/48721; H03M 7/3084
See application file for complete search history.

(56) References Cited

U.S. PATENT DOCUMENTS

| 9,557,294 B2 | 1/2017 | Chen et al. |
| 9,863,904 B2 | 1/2018 | Chen et al. |

(Continued)

FOREIGN PATENT DOCUMENTS

| JP | 08292062 A | 11/1996 |
| JP | 2013-519088 A | 5/2013 |

(Continued)

OTHER PUBLICATIONS

Batzer, Mark A. et al., "Enhanced evolutionary PCR using oligo-nucleotides with inosine at the 3'-terminus," Oxford University Press, Nucleic Acids Research, vol. 19, No. 18, p. 5081 (1991).

(Continued)

*Primary Examiner* — Russell S Negin
(74) *Attorney, Agent, or Firm* — Kilpatrick Townsend and Stockton LLP

(57) ABSTRACT

Techniques described herein relate to systems and methods for parallel DNA molecules sequencing. A preprocessor can receive raw data frames from a sensor chip including 100,000 or more cells, where each raw data frame can include detection signals from the 100,000 or more cells at a given time during the formation of the 100,000 or more cells or during the DNA molecules sequencing using the 100,000 or more cells. The preprocessor can then extract relevant information for determining states of the cells from the raw data frames, generate one or more digested frames that includes the extracted information, and send the digested frames to a processor for processing, such as base determination. Because the number of digested frames sent to the processor is less than a number of the raw data frames and the digested frames include preprocessed data, the amount of data being transferred to the processor and the amount of data processing by the processor can be reduced.

30 Claims, 20 Drawing Sheets

(51) Int. Cl.
*G16B 30/00* (2019.01)
*C12Q 1/6869* (2018.01)
*C12Q 1/68* (2018.01)
*G01N 33/487* (2006.01)
*H03M 7/30* (2006.01)

(56) References Cited

U.S. PATENT DOCUMENTS

| | | | |
|---|---|---|---|
| 2004/0041998 A1* | 3/2004 | Haddad | G06K 9/00033 356/71 |
| 2010/0292101 A1 | 11/2010 | So et al. | |
| 2011/0193249 A1* | 8/2011 | Chen | G01N 33/48721 264/4 |
| 2011/0274349 A1* | 11/2011 | Kalevo | H04N 19/80 382/166 |
| 2012/0020537 A1 | 1/2012 | Garcia et al. | |
| 2014/0134616 A1 | 5/2014 | Davis et al. | |
| 2017/0089858 A1 | 3/2017 | Fernandez-Gomez et al. | |
| 2017/0283866 A1 | 10/2017 | Wahba et al. | |
| 2017/0283867 A1 | 10/2017 | Wahba et al. | |
| 2017/0370902 A1 | 12/2017 | Bajaj | |
| 2017/0370903 A1 | 12/2017 | Mager et al. | |

FOREIGN PATENT DOCUMENTS

| | | | |
|---|---|---|---|
| JP | 2016504593 A | 2/2016 | |
| WO | 02/42496 A2 | 5/2002 | |
| WO | WO-2009076485 A2 * | 6/2009 | C12Q 1/6869 |
| WO | 2011/097028 A1 | 8/2011 | |
| WO | 2014/074727 A1 | 5/2014 | |
| WO | 2014123716 A1 | 8/2014 | |
| WO | WO-2015074005 A1 * | 5/2015 | G01N 21/645 |
| WO | 2016/073318 A1 | 5/2016 | |
| WO | 2016/099673 A1 | 6/2016 | |

OTHER PUBLICATIONS

Horhota, Allen T., et al., "Glycerol Nucleoside Triphosphates: Synthesis and Polymerase Substrate Activities," American Chemical Society, Organic Letters, vol. 8, No. 23, pp. 5345-5347 (2006).

Rossolini, Gian Maria, et al, "Use of deoxyinosine-containing primers vs degenerate primers for polymerase chain reaction based on ambiguous sequence information," Academic Press Limited, Molecular and Cellular Probes, vol. 8, pp. 91-98, (1994).

Ohtsuka, Eiko, et al., "An Alternative Approach to Deoxyoligonucleotides as Hybridization Probes by Insertion of Deoxyinosine at Ambiguous Codon Positions," The American Society of Biological Chemists, Inc., The Journal of Biological Chemistry, vol. 260, No. 5, issue of Mar. 10, pp. 2605-2608, (1985).

International Search Report and Written Opinion from PCT/EP2017/082872 dated Feb. 26, 2018; 12 pages.

* cited by examiner

1700

1710 — Receive a set of data frames from a sensor chip including a plurality of cells, where each data frame includes detection signals from the plurality of cells and corresponds to a different time

1720 — Extract information from the detection signals of the plurality of cells in the set of data frames to obtain digested information for use in determining the states of the plurality of cells

1730 — Generate a group of digested frames that includes the digested information extracted from the set of data frames

1740 — Send the group of digested frames to a processor for use in determining the states of the plurality of cells

FIG. 17

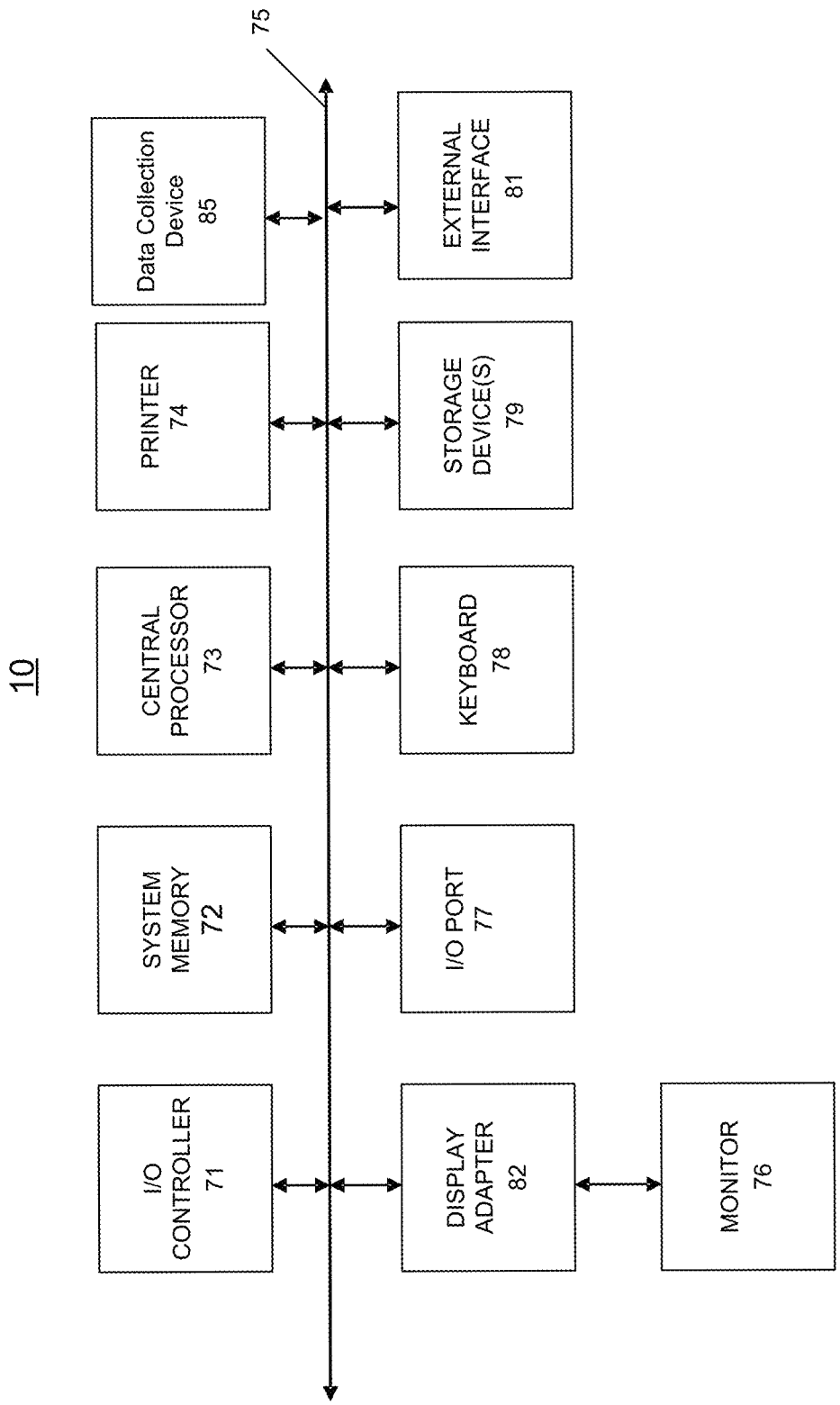

ADAPTIVE NANOPORE SIGNAL COMPRESSION

CROSS-REFERENCES TO RELATED APPLICATIONS

This application claims priority to U.S. Provisional Application No. 62/435,033, filed on Dec. 15, 2016, the entire content of which is incorporated by reference herein for all purposes.

BACKGROUND

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can exist. The size of the current is sensitive to the pore size and which molecule in the nanopore. The molecule can be a particular tag attached to a particular nucleotide, thereby allowing detection of a nucleotide at a particular position of a nucleic acid. A voltage in a circuit including the nanopore can be measured (e.g., at an integrating capacitor) as a way of measuring the resistance of the molecule, thereby allowing detection of which molecule is in the nanopore.

Nanopore-based sequencing sensor chips may be used for DNA sequencing. A nanopore-based sequencing sensor chip can incorporate a large number of sensor cells configured as an array for parallel sequencing. For example, a nanopore-based sequencing sensor chip may include 100,000 or more (e.g., one million or more) cells arranged in a two-dimensional array for sequencing 100,000 or more DNA molecules in parallel. Thus, a large amount of data that includes measurement signals from the 100,000 or more cells may be generated by the sensor chip during each time period of a plurality of time periods.

SUMMARY

The present disclosure relates generally to nanopore-based DNA sequencing, and more specifically, to compressing data generated by a nanopore-based sequencing sensor chip that includes a large number of parallel sequencing sensor cells. Instead of sending all data generated by the sequencing sensor cells for processing, a pre-processing circuit is used to extract relevant information from the data generated by the sequencing sensor cells and forward only the extracted information for further processing to reduce the amount of data being transferred.

In some embodiments, the pre-processing circuit may be used to extract, from the data generated by the sensor chip, relevant information for checking and calibrating the sequencing sensor cells during formation of the sequencing sensor cells and relevant information for determining bases in DNA molecules. Only the extracted information is sent to a processor that can check and calibrate the sequencing sensor cells and/or determine bases in the DNA molecules based on the extracted information. The pre-processing circuit may be configured to extract different information from the data generated by the sensor chip during different phases of cell formation, calibration, and sequencing. In some embodiments, the pre-processing circuit may adaptively extract different information from the data generated by the sensor chip at different times based on request from other components in a sequencing system.

In some embodiments, a method of operating a sequencing system configured to sequence at least 100,000 DNA molecules in parallel is disclosed. The method may include receiving, by a pre-processing circuit, a set of data frames from a sensor chip including a plurality of cells, where each data frame may include detection signals from the plurality of cells and may correspond to a different time. The method may also include extracting information from the set of data frames to obtain digested information for use in determining the states of the plurality of cells. The method may further include generating a group of digested frames that includes the digested information extracted from the set of data frames, and sending the group of digested frames to a processor for use in determining the states of the plurality of cells.

In some embodiments, a device for processing output data from a sensor chip including a plurality of cells is disclose. The device may include a pre-processing circuit and a memory coupled to the pre-processing circuit. The pre-processing circuit may be configured to receive a set of data frames from the sensor chip, where each data frame may include detection signals from the plurality of cells and may correspond to a different time. The device may store at least some of the set of data frames in the memory. The device may extract information from the detection signals of the plurality of cells in the set of data frames to obtain digested information for determining the states of the plurality of cells, generate a group of digested frames that includes the digested information extracted from the set of data frames, and send the group of digested frames to a processor for use in determining the states of the plurality of cells.

These and other embodiments of the invention are described in detail below. For example, other embodiments are directed to systems, devices, and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 17 is a flow chart illustrating an example method of operating a sequencing system configured to sequence a plurality of (e.g., 100,000 or more) DNA molecules in parallel according to certain embodiments.

FIG. 19 shows a block diagram of an example computer system usable with system and methods according to certain embodiments.

DEFINITIONS

Figure 1:
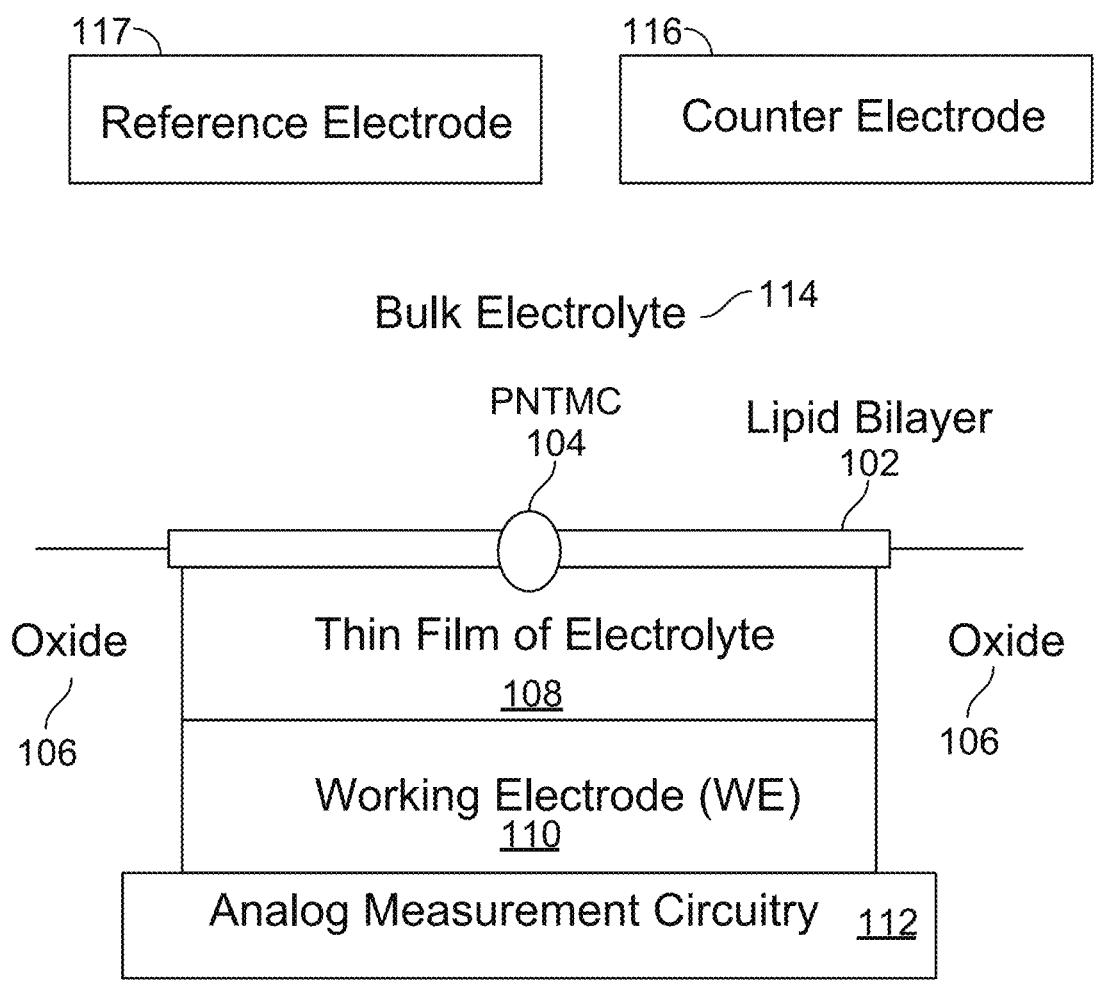
FIG. 1 illustrates an embodiment of a cell in a nanopore based sequencing chip.

"Nucleic acid" may refer to deoxyribonucleotides or ribonucleotides and polymers thereof in either single- or double-stranded form. The term may encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs may include, without limitation, phosphorothioates, phosphoramidites, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The term "nucleotide," in addition to referring to the naturally occurring ribonucleotide or deoxyribonucleotide monomers, may be understood to refer to related structural variants thereof, including derivatives and analogs, that are functionally equivalent with respect to the particular context in which the nucleotide is being used (e.g., hybridization to a complementary base), unless the context clearly indicates otherwise.

"Nanopore" refers to a pore, channel or passage formed or otherwise provided in a membrane. A membrane can be an organic membrane, such as a lipid bilayer, or a synthetic membrane, such as a membrane formed of a polymeric material. The nanopore can be disposed adjacent or in proximity to a sensing circuit or an electrode coupled to a sensing circuit, such as, for example, a complementary metal oxide semiconductor (CMOS) or field effect transistor (FET) circuit. In some examples, a nanopore has a characteristic width or diameter on the order of 0.1 nanometers (nm) to about 1000 nm. Some nanopores are proteins.

The term "bright period" may generally refer to the time period when a tag of a tagged nucleotide is forced into a nanopore by an electric field applied through an AC signal. The term "dark period" may generally refer to the time period when a tag of a tagged nucleotide is pushed out of the nanopore by the electric field applied through the AC signal. An AC cycle may include the bright period and the dark period. In different embodiments, the polarity of the voltage signal applied to a nanopore cell to put the nanopore cell into the bright period (or the dark period) may be different. The bright periods and the dark periods can correspond to different portions of an alternating signal relative to a reference voltage.

The term "signal value" may refer to a value of the sequencing signal output from a sequencing cell. According to certain embodiments, the sequencing signal may be an electrical signal that is measured and/or output from a point in a circuit of one or more sequencing cells e.g., the signal value may be (or represent) a voltage or a current. The signal value may represent the results of a direct measurement of voltage and/or current and/or may represent an indirect measurement, e.g., the signal value may be a measured duration of time for which it takes a voltage or current to reach a specified value. A signal value may represent any measurable quantity that correlates with the resistivity of a nanopore and from which the resistivity and/or conductance of the nanopore (threaded and/or unthreaded) may be derived. As another example, the signal value may correspond to a light intensity, e.g., from a fluorophore attached to a nucleotide being catalyzed to a nucleic acid with a polymerase.

The term "frame" or "data frame" refers to a collection of data that includes at least one data point for each operational cell on a sensor chip. A frame may be a raw frame that includes raw data from each operational cell of the sensor chip at a given time. A frame may also be a digested frame that includes processed data from one or more raw frames. The term "frame map" or "recording frame map" refers to a sequence of frames used to describe a flow of frames that are sent to a processor for processing. A "frame map" may repeat periodically unless otherwise specified. For example, a "$R_1R_2MDR_1M$" recording frame map may indicate a sequence of the first and second raw frames from a bright period of a cycle ($R_1$ and $R_2$), followed by a median (M) frame for the bright period, a decay (D) frame, the first raw frame from a dark period of the cycle ($R_1$), and a median (M) frame for the dark period.

The term "last point delta (LPD)" may refer to the difference between the last sample in a bright period of a cycle and the last sample in the dark period of the cycle. The term "first point delta (FPD)" may refer to the difference between the first sample in a bright period of a cycle and the first sample in the dark period of the cycle. The term "step point delta (SPD) pos/neg or neg/pos" may refer to the difference between the last sample in a bright period and the first sample in the next dark period (pos/neg) or the difference between the last sample in a dark period and the first sample in the next bright period (neg/pos). The term "dark decay delta (DDD)" may refer to the difference between two samples in a dark period of a cycle. The term "wiggle point delta (WPD)" may refer to the difference between the last sample in a bright period and the first sample in the next dark period when a wiggle waveform is applied. The term "X point delta (XPD)" may refer to a difference between any samples (usually excluding LPD). The term "railed" may refer to the minimum or maximum value of the ADC output. For example, for an 8-bit ADC, the railed value may be 0 or 255.

As used herein, a waveform may correspond to a signal and may include the levels (amplitudes), timing, and data associated with the signal. A waveform may be periodic or non-periodic. A waveform may represent an analog signal or a digital signal.

DETAILED DESCRIPTION

Techniques disclosed herein relate to nanopore-based DNA sequencing, and more specifically, to compressing data generated by a nanopore-based sequencing sensor chip that includes a large number of parallel sequencing sensor cells.

In some embodiments, a pre-processing circuit is used to extract, from the data generated by the sensor chip, relevant information for checking and calibrating the sequencing sensor cells during formation of the sequencing sensor cells and relevant information for determining bases in DNA molecules. Only the extracted information is sent to a processor that can check and calibrate the sequencing sensor cells or determine bases in the DNA molecules based on the extracted information. The pre-processing circuit may be configured to extract different information from the data generated by the sensor chip during different phases of cell formation, calibration, and sequencing.

In some embodiments, the pre-processing circuit may adaptively extract different information from the data generated by the sensor chip at different times based on request from other components in a sequencing system.

I. Nanopore System

A nanopore cells in nanopore sensor chip may be implemented in many different ways. For example, in some embodiments, tags of different sizes and/or chemical structures may be attached to different nucleotides in a nucleic acid molecule to be sequenced. In some embodiments, a complementary strand to a template of the nucleic acid molecule to be sequenced may be synthesized by hybridizing differently polymer-tagged nucleotides with the template. In some implementations, the nucleic acid molecule and the attached tags may both move through the nanopore, and an ion current passing through the nanopore may indicate the nucleotide that is in the nanopore because of the particular size and/or structure of the tag attached to the nucleotide. In some implementations, only the tags may be moved into the nanopore. There may also be many different ways to detect the different tags in the nanopores.

A. Nanopore Sequencing Cell

FIG. 1 is a simplified structure illustrating an embodiment of a nanopore cell 100 in a nanopore based sequencing chip, according to certain embodiments. Nanopore cell 100 may include a well formed by dielectrical material, such as oxide 106. A membrane 102 may be formed over the surface of the well to cover the well. In some embodiments, membrane 102 may be a lipid bilayer. A bulk electrolyte 114 that may contain, for example, soluble protein nanopore transmembrane molecular complexes (PNTMC) and the analyte of interest, is placed onto the surface of the cell. A single PNTMC 104 may be inserted into membrane 102 by electroporation. The individual membranes in an array are neither chemically nor electrically connected to each other. Thus, each cell in the array is an independent sequencing machine, producing data unique to the single polymer molecule associated with the PNTMC. PNTMC 104 operates on the analytes and modulates the ionic current through the otherwise impermeable bilayer.

Analog measurement circuitry 112 is connected to a metal working electrode 110 covered by a thin film of electrolyte 108. The thin film of electrolyte 108 is isolated from the bulk electrolyte 114 by the ion-impermeable membrane 102. PNTMC 104 crosses membrane 102 and provides the only path for ionic current to flow from the bulk liquid to working electrode 110. The cell also includes a counter electrode (CE) 116, which is an electrochemical potential sensor. The cell also includes a reference electrode 117.

Figure 2:
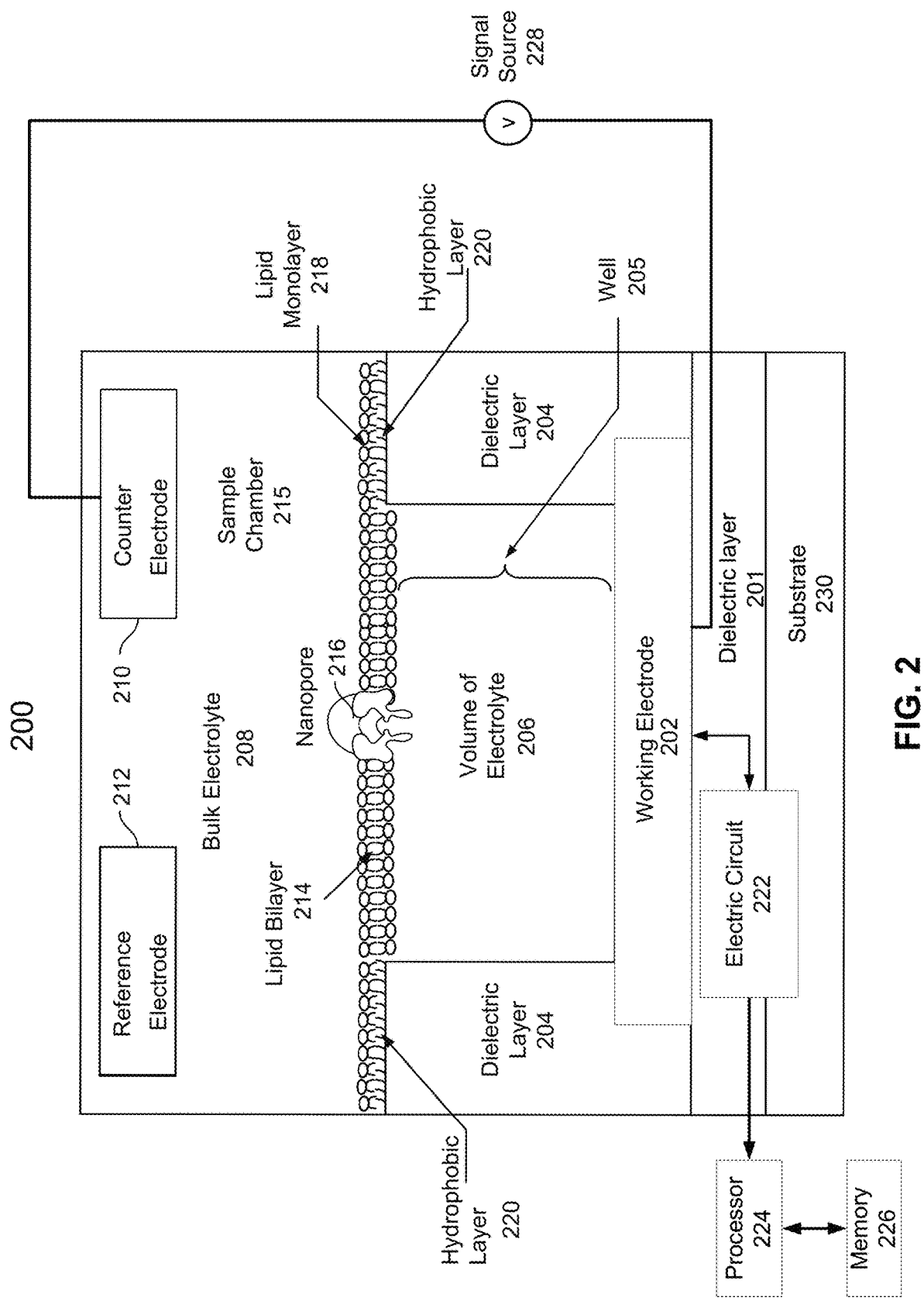
FIG. 2 illustrates an embodiment of a cell in a nanopore based sequencing chip.

FIG. 2 illustrates an embodiment of an example nanopore cell 200 in a nanopore sensor chip that can be used to characterize a polynucleotide or a polypeptide, according to certain embodiments. Nanopore cell 200 may include a well 205 formed of dielectric layers 201 and 204; a membrane, such as a lipid bilayer 214 formed over well 205; and a sample chamber 215 on lipid bilayer 214 and separated from well 205 by lipid bilayer 214. Well 205 may contain a volume of electrolyte 206, and sample chamber 215 may hold bulk electrolyte 208 containing a nanopore, e.g., a soluble protein nanopore transmembrane molecular complexes (PNTMC), and the analyte of interest (e.g., a nucleic acid molecule to be sequenced).

Nanopore cell 200 may include a working electrode 202 at the bottom of well 205 and a counter electrode 210 disposed in sample chamber 215. A signal source 228 may apply a voltage signal between working electrode 202 and counter electrode 210. A single nanopore (e.g., a PNTMC) may be inserted into lipid bilayer 214 by an electroporation process caused by the voltage signal, thereby forming a nanopore 216 in lipid bilayer 214. The individual membranes (e.g., lipid bilayers 214 or other membrane structures) in the array may be neither chemically nor electrically connected to each other. Thus, each nanopore cell in the array may be an independent sequencing machine, producing data unique to the single polymer molecule associated with the nanopore that operates on the analyte of interest and modulates the ionic current through the otherwise impermeable lipid bilayer.

As shown in FIG. 2, nanopore cell 200 may be formed on a substrate 230, such as a silicon substrate. Dielectric layer 201 may be formed on substrate 230. Dielectric material used to form dielectric layer 201 may include, for example, glass, oxides, nitrides, and the like. An electric circuit 222 for controlling electrical stimulation and for processing the signal detected from nanopore cell 200 may be formed on substrate 230 and/or within dielectric layer 201. For example, a plurality of patterned metal layers (e.g., metal 1 to metal 6) may be formed in dielectric layer 201, and a plurality of active devices (e.g., transistors) may be fabricated on substrate 230. In some embodiments, signal source 228 is included as a part of electric circuit 222. Electric circuit 222 may include, for example, amplifiers, integrators, analog-to-digital converters, noise filters, feedback control logic, and/or various other components. Electric circuit 222 may be further coupled to a processor 224 that is coupled to a memory 226, where processor 224 can analyze the sequencing data to determine sequences of the polymer molecules that have been sequenced in the array.

Working electrode 202 may be formed on dielectric layer 201, and may form at least a part of the bottom of well 205. In some embodiments, working electrode 202 is a metal electrode. For non-faradaic conduction, working electrode 202 may be made of metals or other materials that are resistant to corrosion and oxidation, such as, for example, platinum, gold, titanium nitride, and graphite. For example, working electrode 202 may be a platinum electrode with electroplated platinum. In another example, working electrode 202 may be a titanium nitride (TiN) working electrode. Working electrode 202 may be porous, thereby increasing its surface area and a resulting capacitance associated with working electrode 202. Because the working electrode of a nanopore cell may be independent from the working electrode of another nanopore cell, the working electrode may be referred to as cell electrode in this disclosure.

Dielectric layer 204 may be formed above dielectric layer 201. Dielectric layer 204 forms the walls surrounding well 205. Dielectric material used to form dielectric layer 204 may include, for example, glass, oxide, silicon mononitride (SiN), polyimide, or other suitable hydrophobic insulating material. The top surface of dielectric layer 204 may be silanized. The silanization may form a hydrophobic layer 220 above the top surface of dielectric layer 204. In some embodiments, hydrophobic layer 220 has a thickness of about 1.5 nanometer (nm).

Well 205 formed by dielectric layer 204 includes volume of electrolyte 206 above working electrode 202. Volume of electrolyte 206 may be buffered and may include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), manganese chloride ($MnCl_2$), and magnesium chloride ($MgCl_2$). In some embodiments, volume of electrolyte 206 has a thickness of about three microns (μm).

As also shown in FIG. 2, a membrane may be formed on top of dielectric layer 204 and span across well 205. In some embodiments, the membrane may include a lipid monolayer 218 formed on top of hydrophobic layer 220. As the membrane reaches the opening of well 205, lipid monolayer 218 may transition to lipid bilayer 214 that spans across the opening of well 205. The lipid bilayer may comprise or consist of phospholipid, for example, selected from diphytanoyl-phosphatidylcholine (DPhPC), 1,2-diphytanoyl-sn-glycero-3-phosphocoline, 1,2-Di-O-Phytanyl-sn-Glycero-3-phosphocholine (DoPhPC), palmitoyl-oleoyl-phosphatidylcholine (POPC), dioleoyl-phosphatidyl-methylester (DOPME), dipalmitoylphosphatidylcholine (DPPC), phosphatidylcholine, phosphatidylethanolamine, phosphatidylserine, phosphatidic acid, phosphatidylinositol, phosphatidylglycerol, sphingomyelin, 1,2-di-O-phytanyl-sn-glycerol; 1,2-dipalmitoyl-sn-glycero-3-phosphoethanolamine-N-[methoxy(polyethylene glycol)-350], 1,2-dioleoyl-sn-glycero-3-phosphoethanolamine-N-lactosyl; GM1 Ganglioside, Lysophosphatidylcholine (LPC) or any combination thereof.

As shown, lipid bilayer 214 is embedded with a single nanopore 216, e.g., formed by a single PNTMC. As described above, nanopore 216 may be formed by inserting a single PNTMC into lipid bilayer 214 by electroporation. Nanopore 216 may be large enough for passing at least a portion of the analyte of interest and/or small ions (e.g., $Na^+$, $K^+$, $Ca^{2+}$, $Cl^-$) between the two sides of lipid bilayer 214.

Sample chamber 215 is over lipid bilayer 214, and can hold a solution of the analyte of interest for characterization. The solution may be an aqueous solution containing bulk electrolyte 208 and buffered to an optimum ion concentration and maintained at an optimum pH to keep the nanopore 216 open. Nanopore 216 crosses lipid bilayer 214 and provides the only path for ionic flow from bulk electrolyte 208 to working electrode 202. In addition to nanopores (e.g., PNTMCs) and the analyte of interest, bulk electrolyte 208 may further include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), Manganese chloride ($MnCl_2$), and magnesium chloride ($MgCl_2$).

Counter electrode (CE) 210 may be an electrochemical potential sensor. In some embodiments, counter electrode 210 may be shared between a plurality of nanopore cells, and may therefore be referred to as a common electrode. In some cases, the common potential and the common electrode may be common to all nanopore cells, or at least all nanopore cells within a particular grouping. The common electrode can be configured to apply a common potential to the bulk electrolyte 208 in contact with the nanopore 216. Counter electrode 210 and working electrode 202 may be coupled to signal source 228 for providing electrical stimulus (e.g., voltage bias) across lipid bilayer 214, and may be used for sensing electrical characteristics of lipid bilayer 214 (e.g., resistance, capacitance, and ionic current flow). In some embodiments, nanopore cell 200 can also include a reference electrode 212.

In some embodiments, various checks may be made during creation of the nanopore cell as part of verification or quality control. Once a nanopore cell is created, further verification steps can be performed, e.g., to identify nanopore cells that are performing as desired (e.g., one nanopore in each cell). Such verification checks can include physical checks, voltage calibration, open channel calibration, and identification of cells with a single nanopore.

B. Nanopore-Based Sequencing by Synthesis

Nanopore cells in nanopore sensor chip may enable parallel sequencing using a single molecule nanopore-based sequencing by synthesis (Nano-SBS) technique.

Figure 3:
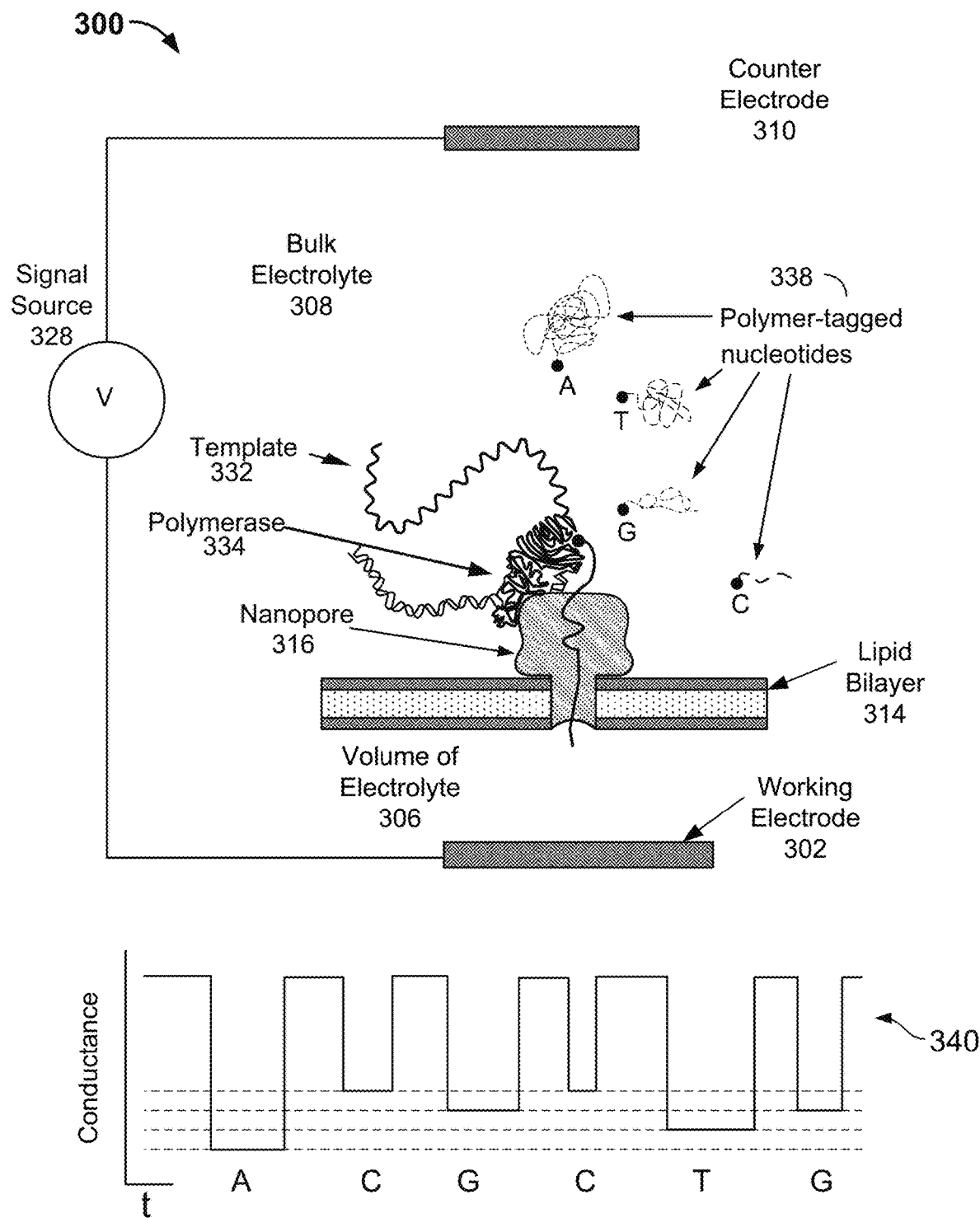
FIG. 3 illustrates an embodiment of a cell performing nucleotide sequencing with the Nano-SBS technique.

FIG. 3 illustrates an embodiment of a nanopore cell 300 performing nucleotide sequencing using the Nano-SBS technique. In the Nano-SBS technique, a template 332 to be sequenced (e.g., a nucleotide acid molecule or another analyte of interest) and a primer may be introduced into bulk electrolyte 308 in the sample chamber of nanopore cell 300. As examples, template 332 can be circular or linear. A nucleic acid primer may be hybridized to a portion of template 332 to which four differently polymer-tagged nucleotides 338 may be added.

In some embodiments, an enzyme (e.g., a polymerase 334, such as a DNA polymerase) may be associated with nanopore 316 for use in the synthesizing a complementary strand to template 332. For example, polymerase 334 may be covalently attached to nanopore 316. Polymerase 334 may catalyze the incorporation of nucleotides 338 onto the primer using a single stranded nucleic acid molecule as the template. Nucleotides 338 may comprise tag species ("tags") with the nucleotide being one of four different types: A, T, G, or C. When a tagged nucleotide is correctly complexed with polymerase 334, the tag may be pulled (loaded) into the nanopore by an electrical force, such as a force generated in the presence of an electric field generated by a voltage applied across lipid bilayer 314 and/or nanopore 316. The tail of the tag may be positioned in the barrel of nanopore 316. The tag held in the barrel of nanopore 316 may generate a unique ionic blockade signal 340 due to the tag's distinct chemical structure and/or size, thereby electronically identifying the added base to which the tag attaches.

As used herein, a "loaded" or "threaded" tag may be one that is positioned in and/or remains in or near the nanopore for an appreciable amount of time, e.g., 0.1 millisecond (ms) to 10000 ms. In some cases, a tag is loaded in the nanopore prior to being released from the nucleotide. In some instances, the probability of a loaded tag passing through (and/or being detected by) the nanopore after being released upon a nucleotide incorporation event is suitably high, e.g., 90% to 99%.

In some embodiments, before polymerase 334 is connected to nanopore 316, the conductance of nanopore 316 may be high, such as, for example, about 300 picosiemens (300 pS). As the tag is loaded in the nanopore, a unique conductance signal (e.g., signal 340) is generated due to the tag's distinct chemical structure and/or size. For example, the conductance of the nanopore can be about 60 pS, 80 pS, 100 pS, or 120 pS, each corresponding to one of the four types of tagged nucleotides. The polymerase may then undergo an isomerization and a transphosphorylation reaction to incorporate the nucleotide into the growing nucleic acid molecule and release the tag molecule.

In some cases, some of the tagged nucleotides may not match (complementary bases) with a current position of the nucleic acid molecule (template). The tagged nucleotides that are not base-paired with the nucleic acid molecule may also pass through the nanopore. These non-paired nucleotides can be rejected by the polymerase within a time scale that is shorter than the time scale for which correctly paired nucleotides remain associated with the polymerase. Tags bound to non-paired nucleotides may pass through the nanopore quickly, and be detected for a short period of time (e.g., less than 10 ms), while tags bounded to paired nucleotides can be loaded into the nanopore and detected for a long period of time (e.g., at least 10 ms). Therefore, non-paired nucleotides may be identified by a downstream processor based at least in part on the time for which the nucleotide is detected in the nanopore.

A conductance (or equivalently the resistance) of the nanopore including the loaded (threaded) tag can be measured via a current passing through the nanopore, thereby providing an identification of the tag species and thus the nucleotide at the current position. In some embodiments, a direct current (DC) signal can be applied to the nanopore cell (e.g., so that the direction at which the tag moves through the nanopore is not reversed). However, operating a nanopore sensor for long periods of time using a direct current can change the composition of the electrode, unbalance the ion concentrations across the nanopore, and have other undesirable effects that can affect the lifetime of the nanopore cell. Applying an alternating current (AC) waveform can reduce the electro-migration to avoid these undesirable effects and have certain advantages as described below. The nucleic acid sequencing methods described herein that utilize tagged nucleotides are fully compatible with applied AC voltages, and therefore an AC waveform can be used to achieve these advantages.

The ability to re-charge the electrode during the AC detection cycle can be advantageous when sacrificial electrodes, electrodes that change molecular character in the current-carrying reactions (e.g., electrodes comprising silver), or electrodes that change molecular character in current-carrying reactions are used. An electrode may deplete during a detection cycle when a direct current signal is used. The recharging can prevent the electrode from reaching a depletion limit, such as becoming fully depleted, which can be a problem when the electrodes are small (e.g., when the electrodes are small enough to provide an array of electrodes having at least 500 electrodes per square millimeter). Electrode lifetime in some cases scales with, and is at least partly dependent on, the width of the electrode.

Suitable conditions for measuring ionic currents passing through the nanopores are known in the art and examples are provided herein. The measurement may be carried out with a voltage applied across the membrane and pore. In some embodiments, the voltage used may range from −400 mV to +400 mV. The voltage used is preferably in a range having a lower limit selected from −400 mV, −300 mV, −200 mV, −150 mV, −100 mV, −50 mV, −20 mV, and 0 mV, and an upper limit independently selected from +10 mV, +20 mV, +50 mV, +100 mV, +150 mV, +200 mV, +300 mV, and +400 mV. The voltage used may be more preferably in the range of 100 mV to 240 mV and most preferably in the range of 160 mV to 240 mV. It is possible to increase discrimination between different nucleotides by a nanopore using an increased applied potential. Sequencing nucleic acids using AC waveforms and tagged nucleotides is described in US Patent Publication No. US 2014/0134616 entitled "Nucleic Acid Sequencing Using Tags," filed on Nov. 6, 2013, which is herein incorporated by reference in its entirety. In addition to the tagged nucleotides described in US 2014/0134616, sequencing can be performed using nucleotide analogs that lack a sugar or acyclic moiety, e.g., (S)-Glycerol nucleoside triphosphates (gNTPs) of the five common nucleobases: adenine, cytosine, guanine, uracil, and thymine (Horhota et al., Organic Letters, 8:5345-5347 [2006]).

In some implementations, additionally or alternatively, other signal values, such as electric current values may be measured and used to identify the nucleotide threaded in a nanopore.

Figure 4:
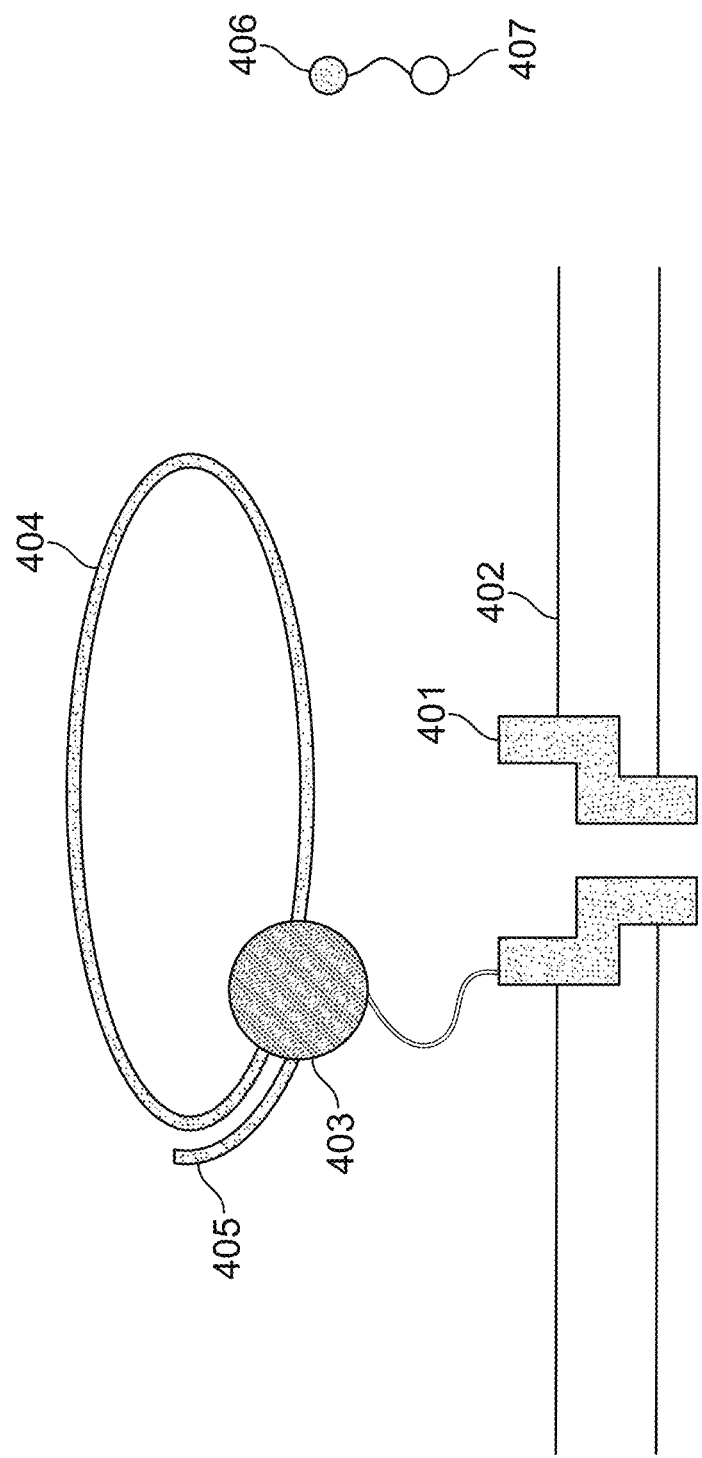
FIG. 4 illustrates an embodiment of a cell about to perform nucleotide sequencing with pre-loaded tags.

FIG. 4 illustrates an embodiment of a cell about to perform nucleotide sequencing with pre-loaded tags. A nanopore 401 is formed in a membrane 402. An enzyme (e.g., a polymerase 403, such as a DNA polymerase) is associated with the nanopore. In some cases, polymerase 403 is covalently attached to nanopore 401. Polymerase 403 is associated with a nucleic acid molecule 404 to be sequenced. In some embodiments, the nucleic acid molecule 404 is circular. In some cases, nucleic acid molecule 404 is linear. In some embodiments, a nucleic acid primer 405 is hybridized to a portion of nucleic acid molecule 404. Polymerase 403 catalyzes the incorporation of nucleotides 406 onto primer 405 using single stranded nucleic acid molecule 404 as a template. Nucleotides 406 comprise tag species ("tags") 407.

Figure 5:
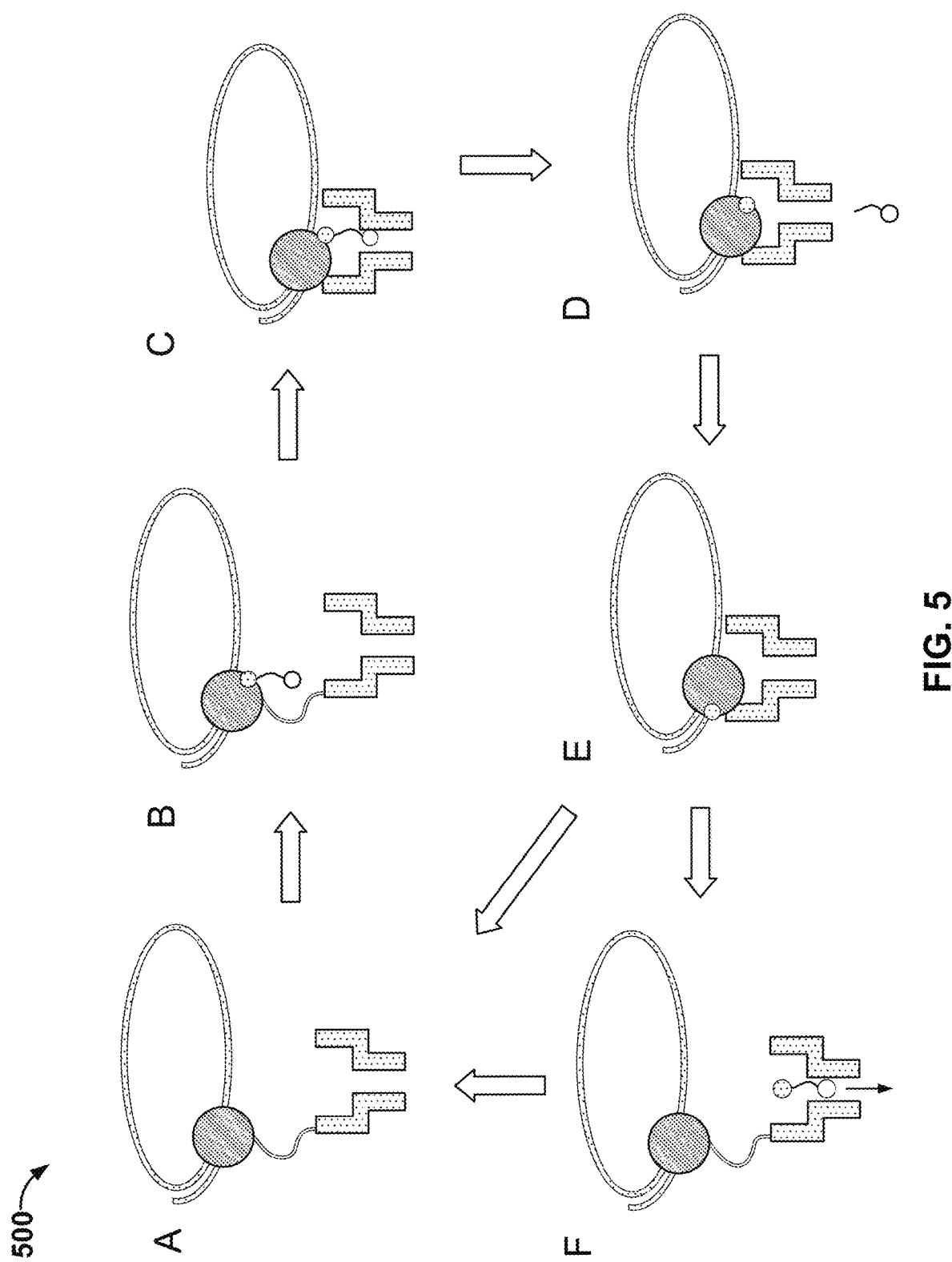
FIG. 5 illustrates an embodiment of a process for nucleic acid sequencing with pre-loaded tags.

FIG. 5 illustrates an embodiment of a process 500 for nucleic acid sequencing with pre-loaded tags. Stage A illustrates the components as described in FIG. 4. Stage C shows the tag loaded into the nanopore. A "loaded" tag may be one that is positioned in and/or remains in or near the nanopore for an appreciable amount of time, e.g., 0.1 millisecond (ms) to 10000 ms. In some cases, a tag that is pre-loaded is loaded in the nanopore prior to being released from the nucleotide. In some instances, a tag is pre-loaded if the probability of the tag passing through (and/or being detected by) the nanopore after being released upon a nucleotide incorporation event is suitably high, e.g., 90% to 99%.

At stage A, a tagged nucleotide (one of four different types: A, T, G, or C) is not associated with the polymerase. At stage B, a tagged nucleotide is associated with the polymerase. At stage C, the polymerase is docked to the nanopore. The tag is pulled into the nanopore during docking by an electrical force, such as a force generated in the presence of an electric field generated by a voltage applied across the membrane and/or the nanopore.

Some of the associated tagged nucleotides are not base paired with the nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 500 as shown in FIG. 5 typically does not proceed beyond stage D. For example, a non-paired nucleotide is rejected by the polymerase at stage B or shortly after the process enters stage C.

In various embodiments, before the polymerase is docked to the nanopore, the conductance of the nanopore can be ~300 picosiemens (300 pS). As other examples, at stage C, the conductance of the nanopore can be about 60 pS, 80 pS, 100 pS, or 120 pS, corresponding to one of the four types of tagged nucleotides respectively. The polymerase undergoes an isomerization and a transphosphorylation reaction to incorporate the nucleotide into the growing nucleic acid molecule and release the tag molecule. In particular, as the tag is held in the nanopore, a unique conductance signal (e.g., see signal 310 in FIG. 3) is generated due to the tag's distinct chemical structures, thereby identifying the added base electronically. Repeating the cycle (i.e., stage A through E or stage A through F) allows for the sequencing of the nucleic acid molecule. At stage D, the released tag passes through the nanopore.

In some cases, tagged nucleotides that are not incorporated into the growing nucleic acid molecule will also pass through the nanopore, as seen in stage F of FIG. 5. The unincorporated nucleotide can be detected by the nanopore in some instances, but the method provides a means for distinguishing between an incorporated nucleotide and an unincorporated nucleotide based at least in part on the time for which the nucleotide is detected in the nanopore. Tags bound to unincorporated nucleotides pass through the nanopore quickly and are detected for a short period of time (e.g., less than 10 ms), while tags bound to incorporated nucleotides are loaded into the nanopore and detected for a long period of time (e.g., at least 10 ms).

Further details regarding the nanopore-based sequencing can be found in, for example, U.S. patent application Ser. No. 14/577,511 entitled "Nanopore-Based Sequencing With Varying Voltage Stimulus," U.S. patent application Ser. No. 14/971,667 entitled "Nanopore-Based Sequencing With Varying Voltage Stimulus," U.S. patent application Ser. No. 15/085,700 entitled "Non-Destructive Bilayer Monitoring Using Measurement Of Bilayer Response To Electrical Stimulus," and U.S. patent application Ser. No. 15/085,713 entitled "Electrical Enhancement Of Bilayer Formation."

II. Measurement Circuitry

Figure 6A:
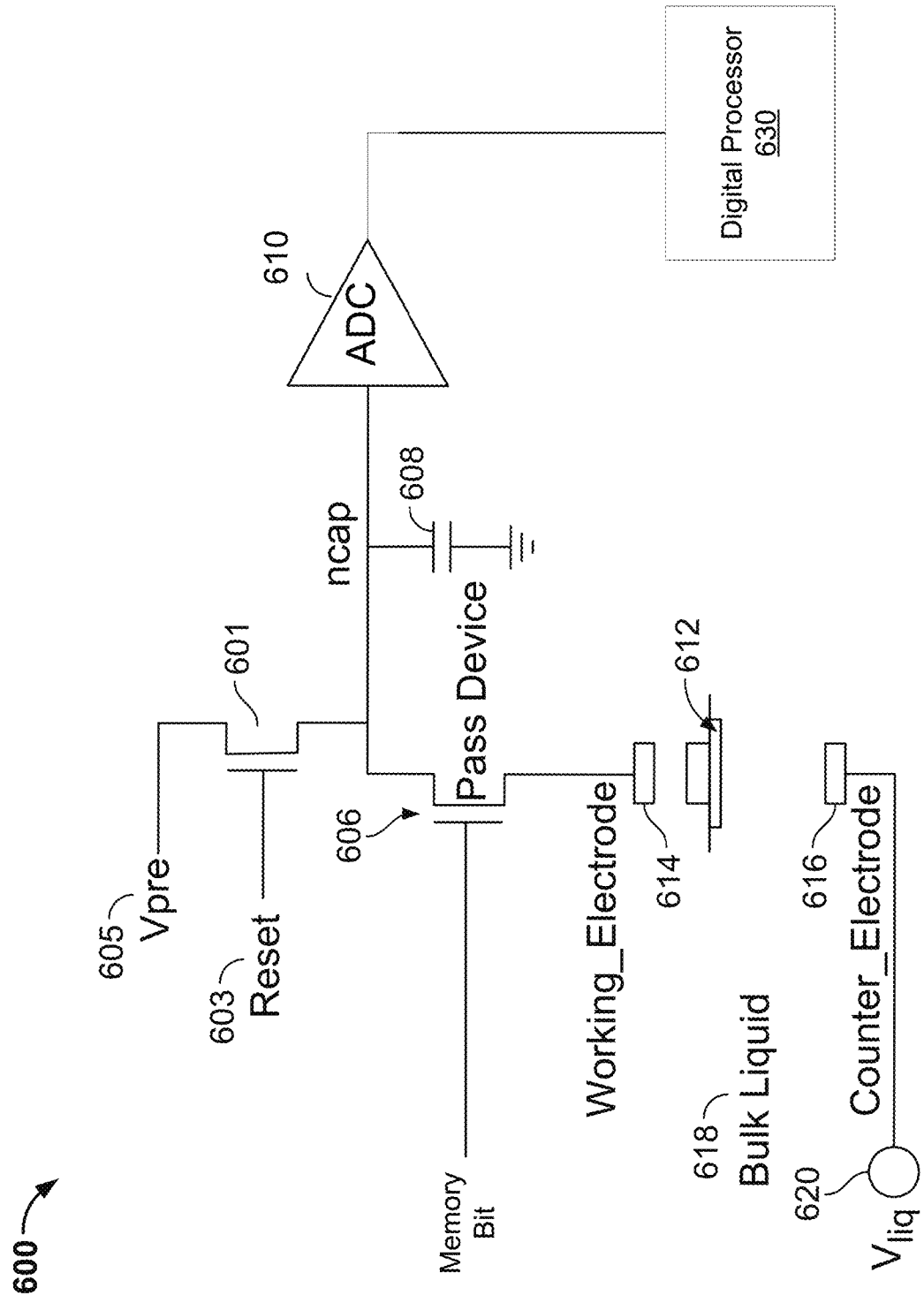
FIG. 6A illustrates an embodiment of a circuitry in a cell of a nanopore based sequencing chip, wherein the circuitry can be configured to detect whether a lipid bilayer is formed in the cell without causing an already formed lipid bilayer to break down.

FIG. 6A shows a lipid membrane or lipid bilayer 612 situated between a cell working electrode 614 and a counter electrode 616, such that a voltage is applied across lipid membrane/bilayer 612. A lipid bilayer is a thin membrane made of two layers of lipid molecules. A lipid membrane is a membrane having a thickness of several molecules (more than two) of lipid molecules. Lipid membrane/bilayer 612 is also in contact with a bulk liquid/electrolyte 618. Note that working electrode 614, lipid membrane/bilayer 612, and counter electrode 616 are drawn upside down as compared to the working electrode, lipid bilayer, and counter electrode in FIG. 1. In some embodiments, the counter electrode is shared between a plurality of cells, and is therefore also referred to as a common electrode. The common electrode can be configured to apply a common potential to the bulk liquid in contact with the lipid membranes/bilayers in the measurements cells by connecting the common electrode to a voltage source $V_{liq}$ 620. The common potential and the common electrode are common to all of the measurement cells. There is a working cell electrode within each measurement cell; in contrast to the common electrode, working cell working electrode 614 is configurable to apply a distinct potential that is independent from the working cell electrodes in other measurement cells.

Figure 6B:
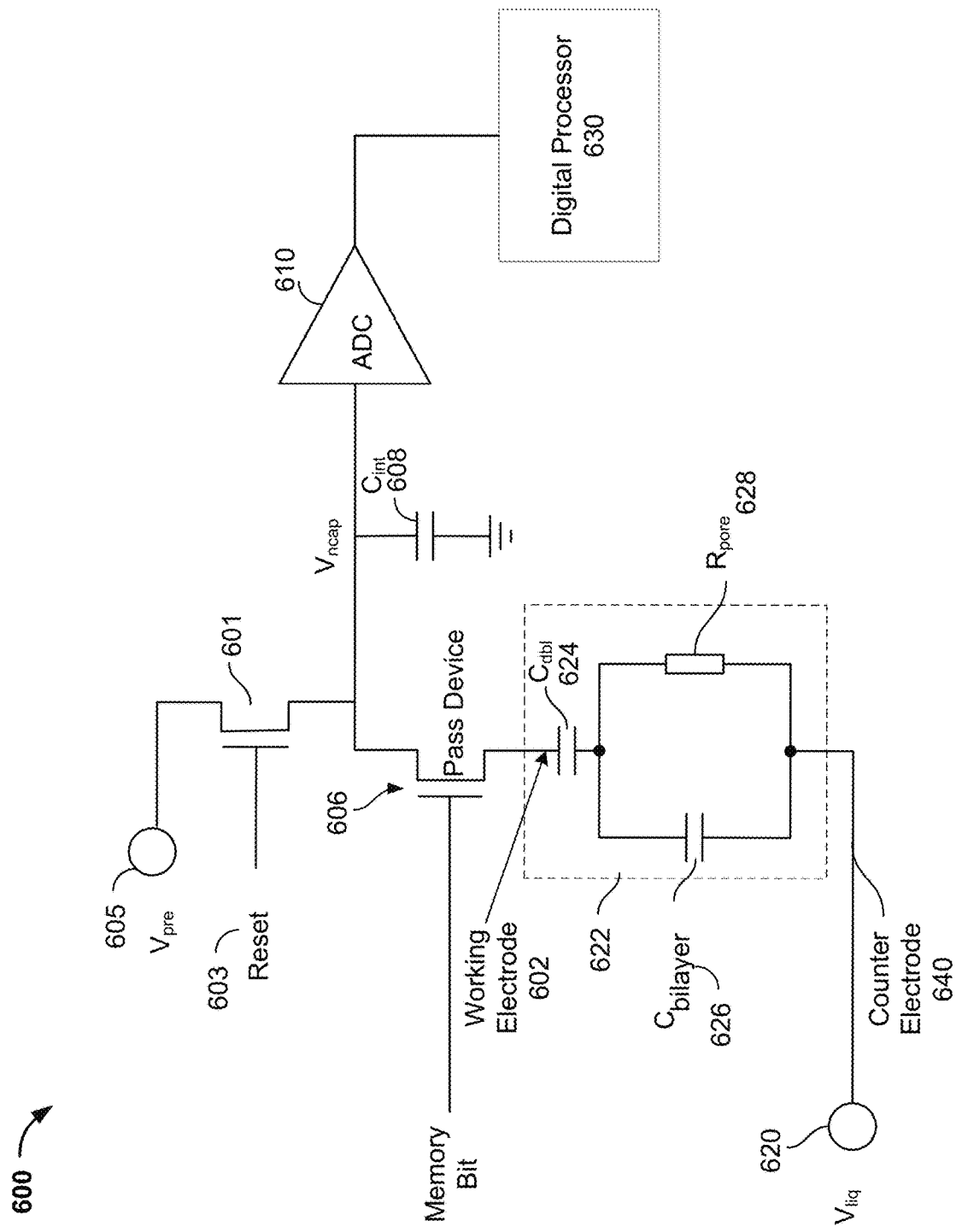
FIG. 6B illustrates the same circuitry in a cell of a nanopore based sequencing chip as that shown in FIG. 6A. Comparing to FIG. 6A, instead of showing a lipid membrane/bilayer between the working electrode and the counter electrode, an electrical model representing the electrical properties of the working electrode and the lipid membrane/bilayer is shown.

FIG. 6B illustrates the same circuitry 600 in a cell of a nanopore based sequencing chip as that shown in FIG. 6A. Comparing to FIG. 6A, instead of showing a lipid membrane/bilayer between the working electrode and the counter electrode, an electrical model representing the electrical properties of the working electrode and the lipid membrane/bilayer is shown.

FIG. 6B illustrates electric circuit 600 (which may include portions of electric circuit 222 in FIG. 2) representing an electrical model in a nanopore cell, such as nanopore cell 200. As described above, in some embodiments, electric circuit 600 includes a counter electrode 640 (e.g., counter electrode 210) that may be shared between a plurality of nanopore cells or all nanopore cells in a nanopore sensor chip, and may therefore also be referred to as a common electrode. The common electrode can be configured to apply a common potential to the bulk electrolyte (e.g., bulk electrolyte 208) in contact with the lipid bilayer (e.g., lipid bilayer 214) in the nanopore cells by connecting to a voltage source $V_{liq}$ 620. In some embodiments, an AC non-Faradaic mode may be utilized to modulate voltage $V_{liq}$ with an AC signal (e.g., a square wave) and apply it to the bulk electrolyte in contact with the lipid bilayer in the nanopore cell. In some embodiments, $V_{liq}$ is a square wave with a magnitude of ±200-250 mV and a frequency between, for example, 25 and 600 Hz. The bulk electrolyte between counter electrode 640 and the lipid bilayer may be modeled by a large capacitor (not shown), such as 100 μF or larger.

FIG. 6B also shows an electrical model 622 representing the electrical properties of a working electrode 602 (e.g., working electrode 202) and the lipid bilayer (e.g., lipid bilayer 214). Electrical model 622 includes a capacitor $C_{bilayer}$ 626 that models a capacitance associated with the lipid bilayer and a resistor $R_{pore}$ 628 that models a variable resistance associated with the nanopore, which can change based on the presence of a particular tag in the nanopore. Electrical model 622 also includes a capacitor $C_{dbl}$ 624 having a double-layer capacitance $c_{dbl}$ and representing the electrical properties of working electrode 602 and the well (e.g., well 205) of the cell. Working electrode 602 may be configured to apply a distinct potential independent from the working electrodes in other nanopore cells.

Pass device 606 may be a switch that can be used to connect or disconnect the lipid bilayer and the working electrode from electric circuit 600. Pass device 606 may be controlled by a memory bit to enable or disable a voltage stimulus to be applied across the lipid bilayer in the nanopore cell. Before lipids are deposited to form the lipid bilayer, the impedance between the two electrodes may be very low because the well of the nanopore cell is not sealed, and therefore pass device 606 may be kept open to avoid a short-circuit condition. Pass device 606 may be closed after lipid solvent has been deposited to the nanopore cell to seal the well of the nanopore cell.

Electric circuit 600 may further include an on-chip integrating capacitor $C_{int}$ 608 ($n_{cap}$). Integrating capacitor $C_{int}$ 608 may be pre-charged by using a reset signal 603 to close switch 601, such that integrating capacitor $C_{int}$ 608 is connected to a voltage source $V_{pre}$ 605. In some embodiments, voltage source $V_{pre}$ 605 provides a constant positive voltage with a magnitude of, for example, 900 mV. When switch 601 is closed, integrating capacitor $C_{int}$ 608 may be pre-charged to the positive voltage level of voltage source $V_{pre}$ 605.

After integrating capacitor $C_{int}$ 608 is pre-charged, reset signal 603 may be used to open switch 601 such that integrating capacitor $C_{int}$ 608 is disconnected from voltage source $V_{pre}$ 605. At this point, depending on the level of voltage source $V_{liq}$, the potential of counter electrode 640 may be at a level higher than the potential of working electrode 602 (and integrating capacitor $C_{int}$ 608), or vice versa. For example, during a positive phase of a square wave from voltage source $V_{liq}$ (e.g., the bright or dark period of the AC voltage source signal cycle), the potential of counter electrode 640 is at a level higher than the potential of working electrode 602. During a negative phase of the square wave from voltage source $V_{liq}$ (e.g., the dark or bright period of the AC voltage source signal cycle), the potential of counter electrode 640 is at a level lower than the potential of working electrode 602. Thus, in some embodiments, integrating capacitor $C_{int}$ 608 may be further charged during the bright period from the pre-charged voltage level of voltage source $V_{pre}$ 605 to a higher level, and discharged during the dark period to a lower level, due to the potential difference between counter electrode 640 and working electrode 602. In other embodiments, the charging and discharging may occur in dark periods and bright periods, respectively.

Integrating capacitor $C_{int}$ 608 may be charged or discharged for a fixed period of time, depending on the sampling rate of an analog-to-digital converter (ADC) 610, which may be higher than 1 kHz, 5 kHz, 10 kHz, 100 kHz, or more. For example, with a sampling rate of 1 kHz, integrating capacitor $C_{int}$ 608 may be charged/discharged for a period of about 1 ms, and then the voltage level may be sampled and converted by ADC 610 at the end of the integration period. A particular voltage level would correspond to a particular tag species in the nanopore, and thus correspond to the nucleotide at a current position on the template.

After being sampled by ADC 610, integrating capacitor $C_{int}$ 608 may be pre-charged again by using reset signal 603 to close switch 601, such that integrating capacitor $C_{int}$ 608 is connected to voltage source $V_{pre}$ 605 again. The steps of pre-charging integrating capacitor $C_{int}$ 608, waiting for a fixed period of time for integrating capacitor $C_{int}$ 608 to charge or discharge, and sampling and converting the voltage level of integrating capacitor by ADC 610 can be repeated in cycles throughout the sequencing process.

A digital processor 630 can process the ADC output data, e.g., for normalization, data buffering, data filtering, data compression, data reduction, event extraction, or assembling ADC output data from the array of nanopore cells into various data frames. In some embodiments, digital processor 630 can perform further downstream processing, such as base determination. Digital processor 630 can be implemented as hardware (e.g., in a GPU, FPGA, ASIC, etc.) or as a combination of hardware and software.

Accordingly, the voltage signal applied across the nanopore can be used to detect particular states of the nanopore. One of the possible states of the nanopore is an open-channel state when a tag-attached polyphosphate is absent from the barrel of the nanopore. Another four possible states of the nanopore each correspond to a state when one of the four different types of tag-attached polyphosphate nucleotides (A, T, G, or C) is held in the barrel of the nanopore. Yet another possible state of the nanopore is when the lipid bilayer is ruptured.

When the voltage level on integrating capacitor $C_{int}$ 608 is measured after a fixed period of time, the different states of a nanopore may result in measurements of different voltage levels. This is because the rate of the voltage decay (decrease by discharging or increase by charging) on integrating capacitor $C_{int}$ 608 (i.e., the steepness of the slope of a voltage on integrating capacitor $C_{int}$ 608 versus time plot) depends on the nanopore resistance (e.g., the resistance of resistor $R_{pore}$ 628). More particularly, as the resistance associated with the nanopore in different states is different due to the molecules' (tags') distinct chemical structures, different corresponding rates of voltage decay may be observed and may be used to identify the different states of the nanopore. The voltage decay curve may be an exponential curve with an RC time constant T=RC, where R is the resistance associated with the nanopore (i.e., $R_{pore}$ 628) and C is the capacitance associated with the membrane (i.e., capacitor $C_{bilayer}$ 626) in parallel with R. A time constant of the nanopore cell can be, for example, about 200-500 ms. The decay curve may not fit exactly to an exponential curve due to the detailed implementation of the bilayer, but the decay curve may be similar to an exponential curve and is monotonic, thus allowing detection of tags.

In some embodiments, the resistance associated with the nanopore in an open-channel state may be in the range of 100 MOhm to 20 GOhm. In some embodiments, the resistance associated with the nanopore in a state where a tag is inside the barrel of the nanopore may be within the range of 200 MOhm to 40 GOhm. In other embodiments, integrating capacitor $C_{int}$ 608 may be omitted, as the voltage leading to ADC 610 will still vary due to the voltage decay in electrical model 622.

The rate of the decay of the voltage on integrating capacitor $C_{int}$ 608 may be determined in different ways. As explained above, the rate of the voltage decay may be determined by measuring a voltage decay during a fixed time interval. For example, the voltage on integrating capacitor $C_{int}$ 608 may be first measured by ADC 610 at time t1, and then the voltage is measured again by ADC 610 at time t2. The voltage difference is greater when the slope of the voltage on integrating capacitor $C_{int}$ 608 versus time curve is steeper, and the voltage difference is smaller when the slope of the voltage curve is less steep. Thus, the voltage difference may be used as a metric for determining the rate of the decay of the voltage on integrating capacitor $C_{int}$ 608, and thus the state of the nanopore cell.

In other embodiments, the rate of the voltage decay can be determined by measuring a time duration that is required for a selected amount of voltage decay. For example, the time required for the voltage to drop or increase from a first voltage level V1 to a second voltage level V2 may be measured. The time required is less when the slope of the voltage vs. time curve is steeper, and the time required is greater when the slope of the voltage vs. time curve is less steep. Thus, the measured time required may be used as a metric for determining the rate of the decay of the voltage $V_{ncap}$ on integrating capacitor $C_{int}$ 608, and thus the state of the nanopore cell. One skilled in the art will appreciate the various circuits that can be used to measure the resistance of the nanopore, e.g., including current measurement techniques.

In some embodiments, electric circuit 600 may not include a pass device (e.g., pass device 606) and an extra capacitor (e.g., integrating capacitor $C_{int}$ 608) that are fabricated on-chip, thereby facilitating the reduction in size of the nanopore-based sequencing chip. Due to the thin nature of the membrane (lipid bilayer), the capacitance associated with the membrane (e.g., capacitor $C_{bilayer}$ 626) alone can suffice to create the required RC time constant without the need for additional on-chip capacitance. Therefore, capacitor $C_{bilayer}$ 626 may be used as the integrating capacitor, and may be pre-charged by the voltage signal $V_{pre}$ and subsequently be discharged or charged by the voltage signal $V_{liq}$. The elimination of the extra capacitor and the pass device that are otherwise fabricated on-chip in the electric circuit can significantly reduce the footprint of a single nanopore cell in the nanopore sequencing chip, thereby facilitating the scaling of the nanopore sequencing chip to include more and more cells (e.g., having millions of cells in a nanopore sequencing chip).

Figure 7:
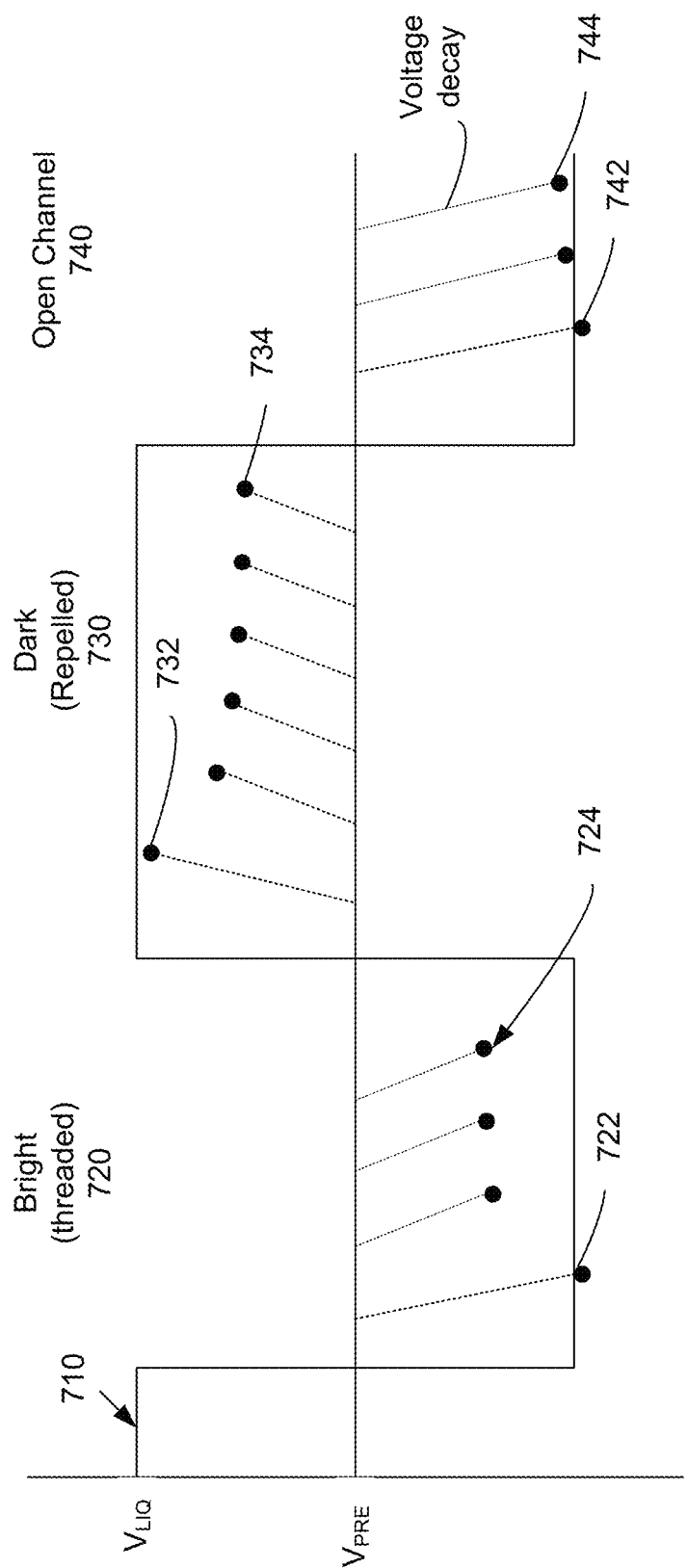
FIG. 7 shows example data points captured from a nanopore cell during bright periods and dark periods of AC cycles.

FIG. 7 shows example data points captured from a nanopore cell during bright periods and dark periods of AC cycles. In FIG. 7, the change in the data points is exaggerated for illustration purpose. The voltage ($V_{PRE}$) applied to the working electrode or the integrating capacitor is at a constant level, such as, for example, 900 mV. A voltage signal 510 ($V_{LIQ}$) applied to the counter electrode of the nanopore cells is an AC signal shown as a rectangular wave, where the duty cycle may be any suitable value, such as less than or equal to 50%, for example, about 40%.

During a bright period 720, voltage signal applied to the counter electrode by voltage source $V_{liq}$ 620 is lower than the voltage $V_{PRE}$ applied to the working electrode, such that a tag may be forced into the barrel of the nanopore by the electric field caused by the different voltage levels applied at the working electrode and the counter electrode (e.g., due to the charge on the tag and/or flow of the ions). When switch 601 is opened, the voltage at a node before the ADC (e.g., at an integrating capacitor) will decrease. After a voltage data point is captured (e.g., after a specified time period), switch 601 may be closed and the voltage at the measurement node will increase back to $V_{PRE}$ again. The process can repeat to measure multiple voltage data points. In this way, multiple data points may be captured during the bright period.

As shown in FIG. 7, a first data point 722 in the bright period after a change in the sign of the $V_{LIQ}$ signal may be lower than subsequent data points 724. This may be because there is no tag in the nanopore (open channel), and thus it has a low resistance and a high discharge rate. In some instances, first data point 722 may exceed the $V_{LIQ}$ level as shown in FIG. 7. This may be caused by the capacitance of the bilayer coupling the signal to the on-chip capacitor. Data points 724 may be captured after a threading event has occurred, i.e., a tag is forced into the barrel of the nanopore, where the resistance of the nanopore and thus the rate of discharging of the integrating capacitor depends on the particular type of tag that is forced into the barrel of the nanopore. Data points 724 may decrease slightly for each measurement due to charge built up at $C_{dbl}$ 624, as mentioned below.

During a dark period 730, voltage signal 710 ($V_{LIQ}$) applied to the counter electrode is higher than the voltage ($V_{PRE}$) applied to the working electrode, such that any tag would be pushed out of the barrel of the nanopore. When switch 601 is opened, the voltage at the measurement node increases because the voltage level of voltage signal 710 ($V_{LIQ}$) is higher than $V_{PRE}$. After a voltage data point is captured (e.g., after a specified time period), switch 601 may be closed and the voltage at the measurement node will decrease back to $V_{PRE}$ again. The process can repeat to measure multiple voltage data points. Thus, multiple data points may be captured during the dark period, including a first point delta 732 and subsequent data points 734. As described above, during the dark period, any nucleotide tag is pushed out of the nanopore, and thus minimal information about any nucleotide tag is obtained, besides for use in normalization.

FIG. 7 also shows that during bright period 740, even though voltage signal 710 ($V_{LIQ}$) applied to the counter electrode is lower than the voltage ($V_{PRE}$) applied to the working electrode, no threading event occurs (open-channel). Thus, the resistance of the nanopore is low, and the rate of discharging of the integrating capacitor is high. As a result, the captured data points, including a first data point 742 and subsequent data points 744, show low voltage levels.

The voltage measured during a bright or dark period might be expected to be about the same for each measurement of a constant resistance of the nanopore (e.g., made during a bright mode of a given AC cycle while one tag is in the nanopore), but this may not be the case when charge builds up at double layer capacitor $C_{dbl}$ 624. This charge build-up can cause the time constant of the nanopore cell to become longer. As a result, the voltage level may be shifted, thereby causing the measured value to decrease for each data point in a cycle. Thus, within a cycle, the data points may change somewhat from data point to another data point, as shown in FIG. 7.

III. Cell Formation and Calibration

Figure 8:
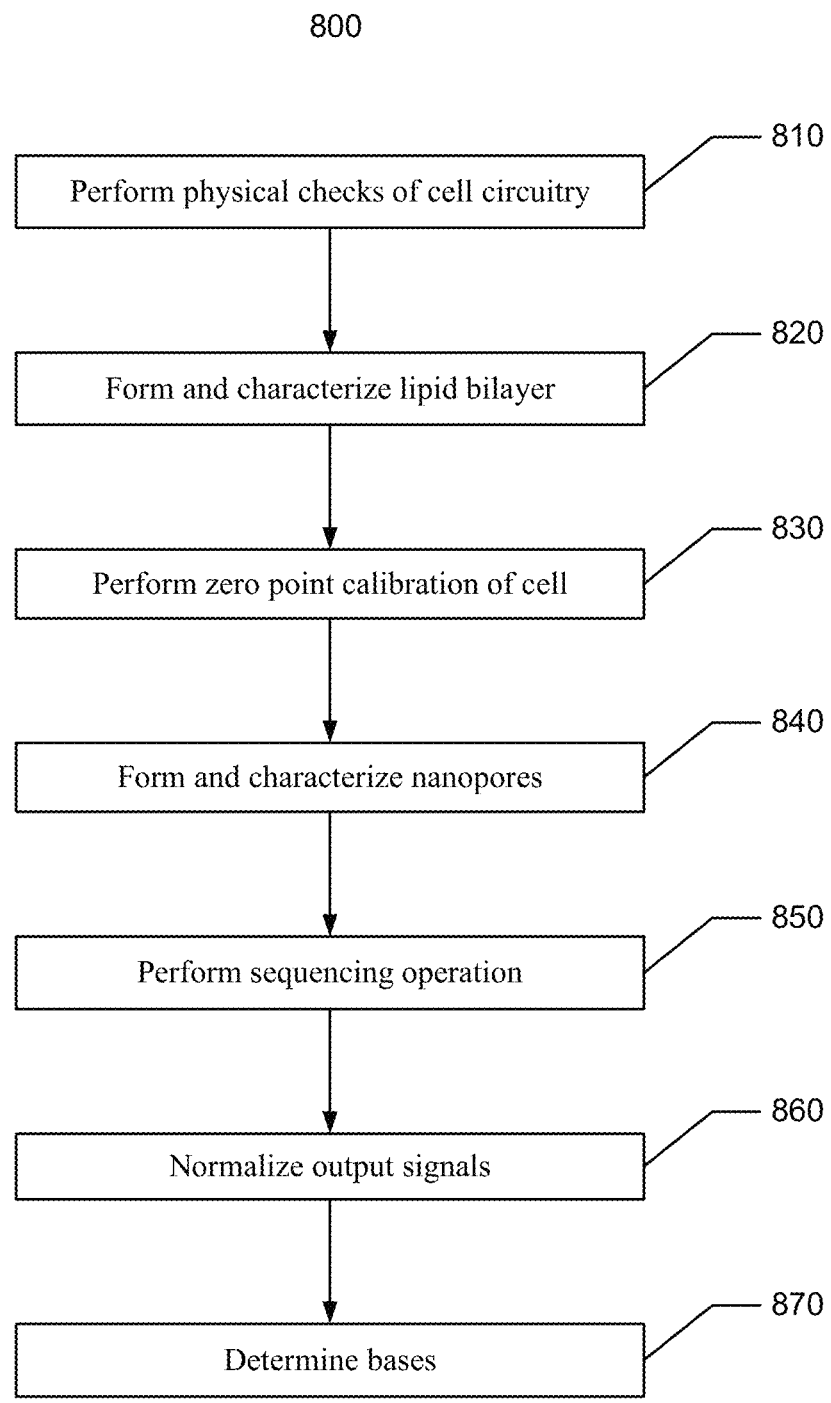
FIG. 8 shows a flow chart illustrating an example method of forming and calibrating nanopore sequencing cells according to certain embodiments.

FIG. 8 is a flow chart illustrating an example method of forming and calibrating nanopore sequencing cells according to certain embodiments. As part of calibration, various checks can be made during creation of the sequencing cell. Once a cell is created, further calibration steps can be performed, e.g., to identify sequencing cells that are performing as desired (e.g., one nanopore in the cell). Once the calibration steps are completed, normalization and sequencing can be performed.

In step 810, physical checks of a cell's circuitry are performed. Some "dry checks" can be performed before any buffer or lipid solution is applied, and some "wet checks" can be performed after buffer and or lipid solution is applied. For example, each cell of the sequencing chip may be checked for an open-circuit (i.e., open state) or short-circuit (i.e., short state). Further description of the physical checks according to certain embodiments can be found below in reference to subsection A of this section.

In step 820, a lipid layer is formed over each cell. According to certain embodiments, the thickness of the lipid layer is monitored during the formation process, and various feedback processes may operate to ensure that the eventual state of the lipid layer is that of a lipid bilayer. For example, if after a first iteration of applying a lipid solution to a cell it is determined that the lipid layer is too thick and is not a bilayer, a thinning procedure may be initiated. Further description of the physical checks associated with the lipid bilayer according to certain embodiments can be found below in reference to subsection A of this section.

In step 830, a zero point voltage calibration is performed for each cell of the sequencing chip. Due to variations in the electronic properties of each cell, each cell can have a different DC offset with zero volts applied to the cell. The DC offset is referred to herein as a "zero point" voltage and, alternatively, as VMzero. For example, there can be manufacturing imperfections or variation between the analog circuitry of different cells in the chip. Thus, the ADC for one cell can have a different voltage bias than the ADC for another cell. Embodiments can perform calibration to account for such variation. Further description of the zero point voltage calibration according to certain embodiments can be found below in reference to subsection B of this section.

In step 840, nanopores are added to each cell, and the cells are characterized to determine how many nanopores per cell have been added. At this step, if too many (more than one) or too few (zero) nanopores have been added to a cell, a feedback process may be initiated to either add or remove nanopore(s) from the cell. According to certain embodiments, cells that are found to have more or less than one nanopore can be deactivated and not used during the sequencing process. Further description of the nanopore characterization according to certain embodiments can be found below in reference to subsections C and E of this section.

In step 850, a sequencing operation is performed, thereby generating output signals from the cells, e.g., as described above in reference to FIGS. 3-7. For example, a tail of a tag may be positioned in the barrel of the nanopore, thereby generating a unique output signal due to the tag's distinct chemical structure and/or size. According to certain embodiments, the output signals may be measured via a current passing through the nanopore, thereby providing an identification of the tag species and thus the nucleotide at a current position in a nucleic acid. In some embodiments, the current or a voltage may be measured by way of an integrating capacitor, e.g., as described above in reference to FIGS. 6A-7. Further description of the sequencing operation according to certain embodiments can be found below in reference to Section IV.

In step 860, the output signals (e.g., voltage and/or current signals) are normalized. Part of this normalization process can involve measuring and or inferring (through the use of an analog circuit model of the cell) a bright mode open channel voltage and using that bright mode open channel voltage as a normalization factor for the output signals. Further description of the normalization process according to certain embodiments can be found below in reference to subsection D. According to certain embodiments, the normalization method may be performed by a digital processor as described above in reference to FIG. 6.

In step 870, one or more processors may determine bases using the normalized output signals. As described in Section IV below, embodiments can determine clusters of voltages for the threaded channels, and use the clusters to determine cutoff voltages for discriminating between different bases using the normalized output signals.

According to certain embodiments, the order of the calibration and normalization checks may be different than that shown in the flow chart of FIG. 8. For example, according to certain embodiments, the calibration and normalization step may be performed once, e.g., after an initial manufacturing processing step is complete (e.g. before formation of the lipid bilayer, after formation of the lipid bilayer, before formation of the nanopore, after formation of the nanopore, etc.). According to certain embodiments, calibration may be done many times over the life of a chip (e.g., at scheduled intervals and/or before every sequencing operation). According to certain embodiments calibration and normalization may be done in an "online" manner, i.e. for each raw data point acquired or every time a group of raw data points is acquired.

Even though sequencing, calibration, and normalization are shown here as separate steps, these steps may be performed together as part of the sequencing operation, i.e., each point or group of points that are acquired during sequencing may be subject to a calibration and normalization step without departing from the scope of the present disclosure. For example, calibration of a sequencing chip can be calibrated before and/or after sequencing starts. The calibration can be performed to ensure that no critical errors exist, where such critical errors might prevent sequencing to be performed in one or more cells. Calibration can also be used to obtain calibration values (e.g., to determine a zero-point voltage) that are used in measuring values (e.g., voltages or currents) or used in analyzing measured values to obtain corrected or normalized voltage values, which can ultimately be used to determine sequence of a nucleic acid.

A. Physical Checks

A dry check can occur before any buffer (e.g., an electrolyte solution) is flowed into the sequencing chip and before a membrane (e.g., a lipid bilayer) is formed over a well. In a dry check, the electrical components of the sequence chip (e.g., for each sequencing cell) are checked to confirm they are functioning properly, e.g., a signal with an expected value (e.g., within a specific range) is received from each well. At this point, there should be no connection between the electrodes (e.g., electrodes 202 and 210), because there is no electrolyte solution in the well or sample chamber. Thus, an "open" state would be expected. If there is a connection (i.e., a short state), then the measured voltage would be outside of an expected range (e.g., a voltage measurement being the same as the reference voltage), thereby indicating that there is something wrong with the cell. In some embodiments, the dry check may be performed using the wiggle point delta (WPD) or step point delta (SPD). As defined above, the step point delta (SPD) may be the difference between the last date point in a bright period and the first data point in the next dark period (i.e., SPD pos/neg) or the difference between the last data point in a dark period and the first data point in the next bright period (SPD neg/pos). The wiggle point delta (WPD) may be the difference between the last data point in a bright period and the first data point in the next dark period when a wiggle waveform is applied. Thus, a WPD or SPD greater than a threshold value may indicate that the cell is in a short state, where the two electrodes are electrically connected even though there is no electrolyte solution between the two electrodes, and thus some electrical components of the cell may be defective (e.g., shorted). In some embodiments, other parameters, such as the first point delta (FPD) or last point delta (LPD), may be used for the dry check.

In a wet check, a buffer is flowed over the surface of the chip. This check can make sure that there is a connection (e.g., a short) between the electrodes through the buffer. An open state (i.e., no connection between the electrodes) may indicate that the corresponding cell may have some defects. In some embodiments, as in the dry check, the wet check may be performed using the wiggle point delta (WPD) or step point delta (SPD). For example, a WPD or SPD lower than a threshold value may indicate that the cell is in an open state, where the two electrodes are electrically disconnected even though the electrolyte solution has been applied between the two electrodes, and thus some electrical components of the cell may be defective (e.g., open). In some embodiments, other parameters, such as the first point delta (FPD) or last point delta (LPD), may be used for the dry check.

In a lipid (cover) layer check, a solution can be flowed over the chip. The solution can be an organic solvent with the lipid dissolved in it. At the end of that process, each well should have a plug of the solvent and lipid. There should be no (or minimal) electrical connection between the electrodes at this point as the lipid layer would be very thick so as to block the flow of the ions in the solution.

A cell can start with a relatively thick lipid layer, which is thinned to form a lipid bilayer. In a thinning procedure, the ADC value can be measured for each cell to determine cells where the lipid layer is too thick, and the bilayer can be thinned. U.S. patent application Ser. No. 15/085,713 describes an electrical lipid-thinning stimulus to thin the lipid layer.

After thinning, there can be a two-molecule-thick lipid bilayer that acts as a membrane to cover the well. In practice, any water-permeable membrane may be used. On the edges of the lipid bilayer is an annulus, an anchoring ring of solvent. The annulus can act as a reservoir of lipids for the bilayer.

The thickness of the lipid layer may be measured using the first point delta (FPD), which corresponds to the difference between the first measured voltage level in a bright period in a cycle and the first measured voltage level in a dark period in the cycle. For example, the FPD may be the difference between the high first points shown in FIG. 7. The first point delta is proportional to the capacitance of the bilayer, and the bilayer thicknesses is proportional to capacitance. When the lipid layer is thick (e.g., microns), the capacitance is small. By the time the thickness shrinks down to about 4 nm, the capacitance is something measurable, e.g., on the order of 100 femtofarads. A bilayer has a deterministic thickness, based on the molecules used, with some small differences based on how the molecules of the bilayer are arranged and how much solvent remains. According to certain embodiments, the thickness of the lipid bilayer may be from 4.2 to 4.3 nm. The capacitance of the bilayer (or other membrane) is proportional to the lateral area, which depends on how much annulus exists. Thus, the FPD can provide whether the bilayer exists and how close to the edge the bilayer has formed. In some embodiments, other parameters, such as the WPD, may be determined from the measured data points to perform the lipid (cover) layer check.

In some embodiments, a feedback mechanism in the system can be used to further thin the lipid layer. To thin the lipid layer, a lateral pressure can be applied (e.g., flowing buffer at high velocity across top of the lipid layer). As another example, one can turn on the AC signal to apply an AC bias, which can effectively shake the layer back and forth until it achieves the energetically stable state of the bi-layer. Such a procedure can remove any local minimum in the formation process of the lipid bilayer.

The feedback can act by measuring the FPD over time and adjusting the feedback. The cells with a sufficiently small FPD (e.g., below a threshold) can have actions performed to thin that particular cell. Such a process can continue until at least a specified percentage of cells (e.g., 70%) have a usable bilayer. In some embodiments, the WPD may be determined from the measured data points to provide the feedback.

B. Voltage Calibration

To calibrate the system for different voltages, a zero-point voltage of each cell (also referred to herein as VMzero) can be determined. For electronic reasons, each cell can have a different DC offset. For example, there can be manufacturing imperfections or variations between the analog circuitry of different cells in the chip. Also, a bias can be built into the system for electrochemical reasons. Due to such manufacturing variability, one electrode can be slightly different than another. This can introduce an offset from cell to cell. In addition, the surface chemistry of the electrodes may make them act as batteries, and thus each cell may have a slightly different potential, which can contribute to the VMzero for each cell. According to certain embodiments, a net effect is that the measured ADC signal is pushed up or down, depending on the value of VMzero. Embodiments can perform a calibration to account for such variation between cells.

Figure 9:
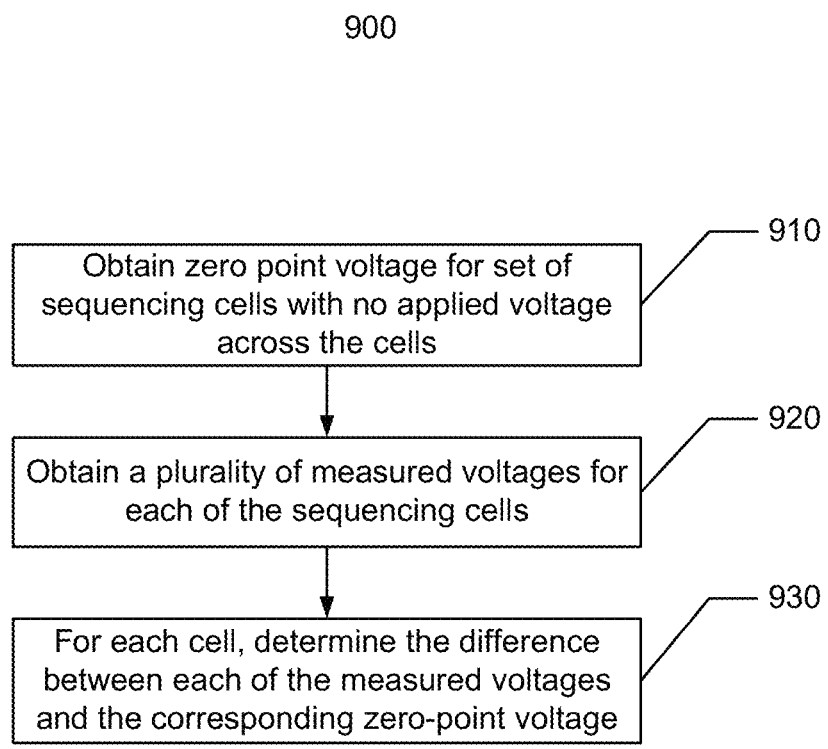
FIG. 9 shows a flow chart illustrating an example method of calibrating nanopore sequencing cells for a sequencing chip according to certain embodiments.

FIG. 9 is a flow chart illustrating an example method 900 of calibration of nanopore sequencing cells for a sequencing chip according to certain embodiments. Method 900 can be performed at various times, e.g., before a membrane has been formed, after a membrane has been formed (but before a pore is inserted), and/or after a pores have been inserted into the cells. This calibration can be performed at multiple times in a calibration process, with different values for VMzero being obtained and used for a given stage.

In step 910, a zero point voltage (also referred to herein as VMzero) is obtained for each cell of the sequencing chip. In some embodiments, VMZero is measured by the ADC with zero voltage applied to the cell (e.g., no pathway for current flow). Such a state of zero applied voltage can be achieved in various ways, e.g., by disconnecting the working electrode and/or the counter electrode or by having both electrodes be at a same voltage. In this manner, each ADC may receive a different floating voltage. Furthermore, the conversion from the analog value to the digital can vary from ADC to ADC. According to certain embodiments, the measured set of VMzeros, one for each cell, can be stored in memory. These stored values can be used to calibrate (i.e., remove the offset from) each cell, thereby ensuring that the ADC measurements of both bright and/or dark period voltages are comparable from cell to cell. As described above, the zero point voltage for each cell can be measured by an ADC, e.g., ADC 610 shown in FIG. 6.

The sequencing chip may include thousands or even millions of cells, and thus thousands or even millions of zero point voltages can be measured. According to certain embodiments, the zero point voltages may be measured and stored in memory before the nanopores are inserted into the lipid bilayers of each cell. In some embodiments, the memory may be integrated onto the sequencing chip or may be an external memory store that is operatively connected to the sequencing chip, e.g., such as any form of computer memory, as described below in reference to FIG. 13. Alternatively or additionally, the zero point voltages may be measured after the nanopores are inserted into the lipid bilayers of each cell. As a further example, the zero point voltages may be measured once for each chip as part of a characterization or calibration step or may be measured multiple times over the lifetime of the chip. For example, VMzero may change over time as the capacitance of the double layer capacitor changes, and thus may be measured before and/or after a sequencing run to ensure that the system is calibrated properly.

In step 920, after the nanopores have been inserted into the lipid bilayers, a sequencing operation may be performed and a plurality of measured voltages may be obtained (e.g., by the ADCs of the sequencing chip). The sequencing may be performed during the application of an alternating signal across each cell of the chip. The process of obtaining voltage data in this manner is described above in reference to FIGS. 3-5.

In step 930, the obtained voltage values are corrected using the stored VMzero values. For example, according to certain embodiments, a difference between a cell's measured values and its VMzero value can be computed, e.g., by a digital processor 430 in FIG. 4. More specifically, a set of corrected or calibrated voltage values can be obtained for each cell by subtracting that cell's VMzero from the measured voltage values.

Accordingly, a zero point voltage value (e.g., as VMzero) can be determined for each cell and used to optimize the dynamic range of the ADC. For example, an ADC can provide a specified data range, e.g., an 8-bit unsigned range (0 to 255). The difference between the digital values are controlled by the manufacturing of the ADC, but the specific analog range can be varied (e.g., as controlled by an ADC reference voltage) to correspond to an expected range of the analog voltage for the sequencing cells, taking into account the cell-specific VMzero. The zero value for the ADC need not correspond to zero volts, as the relative voltages is what is used.

In one embodiment, there are two reference voltages that set the bottom and the top of the ADC voltage range. The two voltages can be of different sign. The reference voltages can be set externally. The reference voltages can be changed as different biochemistry is used. The actual signal should be within the reference range, and ideally take up most of that reference range. According to certain embodiments, knowledge of the measured VMzero for each cell can may be used to set the reference voltages for each cell independently. This can ensure that the full dynamic range of the ADC is being used, thereby minimizing quantization noise.

An offset can also occur as a result of charge that is injected to circuit 600 via switch 601 of FIG. 6. Switch 601 is used for resetting the voltage on integrating capacitor $C_{int}$ 608 in order to take a new measurement using the ADC. Each time the switch closes, an amount of charge is injected into the circuit for that cell. For the charge injection, there is a transfer of certain number of electrons from a source to the drain, thereby dumping a certain amount of charge into the system. The charge distributes among the capacitors, which creates an offset. The offset would be acceptable if it was constant, but it is not constant.

Examples for why such a charge injection offset can vary are as follows. Over time, the surface area of the bilayer can become larger or smaller bilayer (e.g., by the annulus at the edges creeping in and out). This change can cause a ratio of the capacitance of the bilayer to change relative to the capacitance the integrating capacitance (e.g., 608). This ratio affects the time constant of the circuit, and thus what the measured voltage after a specific amount of time, as can be measured by the ADC. If the ratio is determined only once, this ratio value can be become outdated, and thus incorrect. Embodiments can use the magnitude of the charge injection, the capacitance of the bilayer, and how it is changing to determine a normalization to compensate for the charge injection offset.

Using FIG. 6 as an example, the switch 601 resets the voltage of the system, after which an ADC value is measured at a specified amount of time after the switch 601 is opened. The resetting and the measuring is repeated. As the switch is non-ideal, every time the switch 601 close, some charge is injected into the circuit. Charge builds up on $C_{bilayer}$ 626, thereby causing the baseline voltage to change as charge builds up on $C_{bilayer}$.

When the charge is injected, the charge is distributed in the circuit. The primary places are $C_{bilayer}$ 626 and integrating capacitor $C_{int}$ 608. The ratio of the charge between the two capacitors depends on the size of the bilayer. The offset of a particular cell changes over time, as the voltage changes on integrating capacitor $C_{int}$ 608. If the ratio stayed the same, then it would not change the measured offset, as it would stay the same over time. But, as $C_{bilayer}$ 626 changes, different amounts of charged will be injected to $C_{bilayer}$ 626 and integrating capacitor $C_{int}$ 608, thereby changing the offset. Such a problem would not exist if the capacitances did not change over time, as is typical for semiconductor capacitors, but is not true for biochemical elements that act as capacitors.

As a solution, $C_{bilayer}$ 626 can be measured over time. The capacitance of integrating capacitor $C_{int}$ 608 would not typically change over time, as it can be a semiconductor element. The charge can be quantified at the beginning of a sequencing run, and may be different for each cell. This charge can be determined as part of calibration, e.g., as part of determining VMzero. $C_{bilayer}$ 626 can be measured using the first point delta, which is the difference in the first voltages measured for bright and dark modes after a cycle switch in polarity, e.g., of a square wave. There is a relationship between the first point delta (FPD) and $C_{bilayer}$ 626. Such a relationship can be constant from cell to cell.

Accordingly, the change in FPD can be used to determine the change in the offset of VMzero. The relationship is based on the amount of charge injected into the system as measured for a beginning cycle, the value of integrating capacitor $C_{int}$ 608 for the cell, the initial measurement of $C_{bilayer}$ 626, and the change in FPD of the beginning cycle.

In some embodiments, the following technique can be used to determine a change to VMzero as a result of the charge injection. The charge q=C*V, where q is charge, C is capacitance and V is voltage. C=$C_{bilayer}$ 626+$C_{ncap}$ (integrating capacitor $C_{int}$ 608). V=q/($C_{bilayer}$ $C_{ncap}$), and the change in voltage due to a changing bilayer cap is: dV=q (1/($C_{bl\_new}$+$C_{ncap}$)−1/($C_{bl\_old}$+$C_{ncap}$)). This change in voltage can be used to modify an ADC value before other normalization, e.g., to compensate for gain drift or baseline shift.

C. Nanopore Insertion

Nanopores can be inserted into the lipid bilayer a number of different ways. For example, if relying on force of pressure in the chip to randomly diffuse the pores into the membranes, then the proportion would be governed by binomial distribution. In such a situation, many cells would have zero nanopores, some would have one, some would have two, and the majority would not have just one. However, according to certain embodiments, just one nanopore per cell is best for sequencing. If there are more than one nanopore per cell, e.g., two nanopores per cell, then the signal from the pore will be some combination of the two signals from the two pores, which can cause the levels to have error, as such a system has a different equivalent circuit than a single pore cell. Furthermore, the combined signal would results from tags entering the nanopore at different times, making it difficult to know which base to call at a given time.

According to certain embodiments, electroporation can be used to insert the nanopores into the bilayer. Electroporation applies a square wave across the bilayer to stress it. Too high a voltage would pop the lipid layer. But a suitable voltage can provide a tear where the nanopore can be inserted more easily.

As mentioned above, it is beneficial for each cell to have exactly one nanopore. To accomplish this, according to certain embodiments a diagnostic measurement can be taken for each cell before, during, and after the electroporation signal is applied, e.g., a voltage value akin to an open channel measurement described above in reference to FIGS. 6A-7 can be measured. The measured value can then be then analyzed to determine whether the measured value corresponds to a value that would be expected for a cell having only one nanopore. A single nanopore may be detected by tracking a voltage changes during the electroporation process, and if the voltage changes significantly then it is assumed that proration has successfully completed. In some embodiments, the difference between two points in a dark period of a cycle (i.e., dark decay delta (DDD)) and/or the LPD may be used to perform the check during the electroporation process.

When a nanopore is observed to have been added to a cell, the electroporation process can be stopped for that well. This can be done independently for each well. The above process can be used in combination with a diagnostic technique that employs a voltage histogram/distribution of the open channel voltages for all the cells across the sequencing chip to identify an open-channel voltage, or range of open channel voltages, that indicate a single nanopore cell. For those cells that do not have any pores after the first electroporation step, the electroporation may be repeated.

D. Open Channel Calibration

After electroporation, the output voltage of a cell with no tag in place can be measured to determine the initial voltage of the cell. As described above in reference to FIGS. 6A-7, this measured ADC value is referred to as an open channel voltage. The value of the open channel voltage can be used in normalization, as described later. In addition, the value of the open channel can be used to identify cells with a single nanopore, as described in the next section.

According to certain embodiments, as part of the open channel calibration process, the cycle decay shape can also be determined, as described above in reference to FIGS. 6A-7. For example, in response to an alternating signal ($V_{LIQ}$) provided to the counter electrodes, an ADC may measure an output voltage on an integrating capacitor, e.g., integrating capacitor $C_{int}$ 608 of FIG. 6B. As shown in FIG. 7, the voltage measured by the ADC does not exactly track the square wave drive signal, but rather can show a decay over the bright or dark periods within each cycle of the drive signal $V_{LIQ}$ as a result of the buildup of charge on $C_{dbl}$. According to certain embodiments, the resulting decay shape of each period within one AC cycle can be measured as part of the open channel calibration process. The initial value of the open channel can help to determine the expected value for the channels corresponding to different molecules (e.g., four different bases).

In some embodiments, the open channel calibration can be performed for each cell of the sequencing chip immediately after the poration process is complete. The open channel calibration process can also leverage the presence of open channel data during a sequencing operation, and thus can be performed as part of a preprocessing step during the data normalization process described in detail below.

The ADC values measured during sequencing can be normalized to provide greater accuracy. In some embodiments, the voltage level data that is acquired during a bright period of the AC drive voltage (referred to herein as the "bright mode voltages" or alternatively as the "bright period voltage") are normalized. For example, the bright mode voltages can be normalized by dividing each measured bright mode data point by the bright mode voltage of the cell when the nanopore is in an unthreaded state, referred to herein as the "open channel voltage" or "bright mode open-channel voltage." By normalizing the bright mode voltage level data, the dynamic range of the raw ADC measurements is rescaled to a normalized range, generally to provide a range between 0 and 1, although values greater than 1 are possible, depending on the specific value used for bright mode open-channel voltage.

Normalization can allow compensating for changes to the system, e.g., changes in the electrical properties of a sequencing cell. For instance, the capacitances of circuit 600 may change over time. For example, the capacitance of capacitor $C_{bilayer}$ 626 because of physical changes in the bilayer area or thickness, e.g., at the edges of a well, where such change is referred to as gain drift. As another example, charge can build up in the cell as a result of differences in charge transfer between bright periods and dark periods, which is referred to as baseline shift (and sometimes fast baseline shift). A slow baseline shift can be caused by variability in the measurements circuit and changes in the electrical properties of the bilayer membrane. These examples are described in more detail below.

Such changes can affect the values measured for the exact same state, thereby causing instabilities. However, normalization can compensate for such changes to provide normalized values (e.g., voltages or currents) that are stable over time, thereby allowing greater accuracy in determining the sequence of a nucleic acid.

E. Identification of Wells with Single Nanopore

As mentioned above, it is desired that each cell of the sequencing chip have only one nanopore. According to certain embodiments, the cells with one nanopore can be identified by a statistical analysis of the magnitudes of the open channel voltages (e.g., the measured ADC value during bright or dark mode, without a tag present in the nanopore). A histogram (or distribution) of the measured voltages can be computed by binning the measured voltages and counting the number of cells having voltages that fall within a particular voltage bin. The histogram can be analyzed to determine the largest amplitude peak, i.e. the most common voltages amongst the cells of the chip can be determined. The largest amplitude peak can be constrained to be within a certain expected range, which may be done by excluding a final bin of the histogram, which includes all measured voltages higher than a specified value.

According to certain embodiments, the most common voltages should correspond to the single nanopore cells, particularly when the electroporation process was monitored and subject to a feedback mechanism. Generally, the parameters of the poration process may be previously tuned such that for most cells, only a single pore will form, with a relatively small population forming more than one pore or no pore at all. In another embodiment, the second largest amplitude peak can be used as the peak corresponding to cells having only one nanopore, while the largest amplitude peak may correspond to cells with bare bilayers, i.e., zero nanopores.

Figure 10:
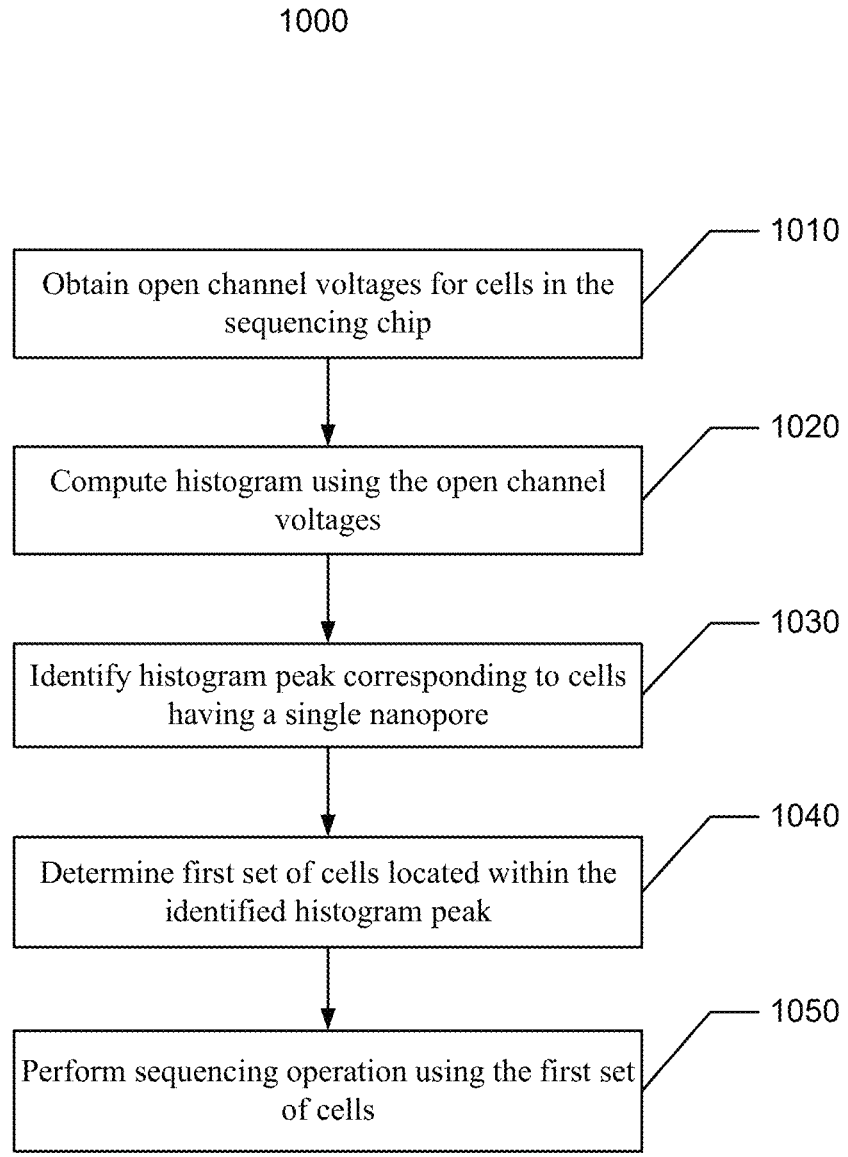
FIG. 10 shows a flow chart illustrating an example method of characterizing the number of nanopores in the cells of a sequencing chip according to certain embodiments.

FIG. 10 is a flow chart illustrating an example method 1000 of characterizing the number of nanopores in the cells of a sequencing chip according to certain embodiments. Method 1000 may be performed after a pore insertion process (or at least after an initial stage of pore insertion). Method 1000 may be performed by, for example, digital processor 630, processing units or processor described below in FIG. 13 and FIG. 19, and/or any control logic coupled with the circuits of the sequencing cell, including forward connections for the control logic to provide control signals (e.g., to control further poration steps).

In step 1010, open channel voltages are obtained for cells in the sequencing chip. For example, the open channel voltages can be obtained in a similar manner to the voltages described above in reference to FIG. 7 and elsewhere in this disclosure. The obtaining of the open channel voltages may be achieved by receiving the voltages from the sequencing chip at a logic system, e.g., an FPGA, ASIC, or programmable processor.

Figures 11A, 11B, 11C:
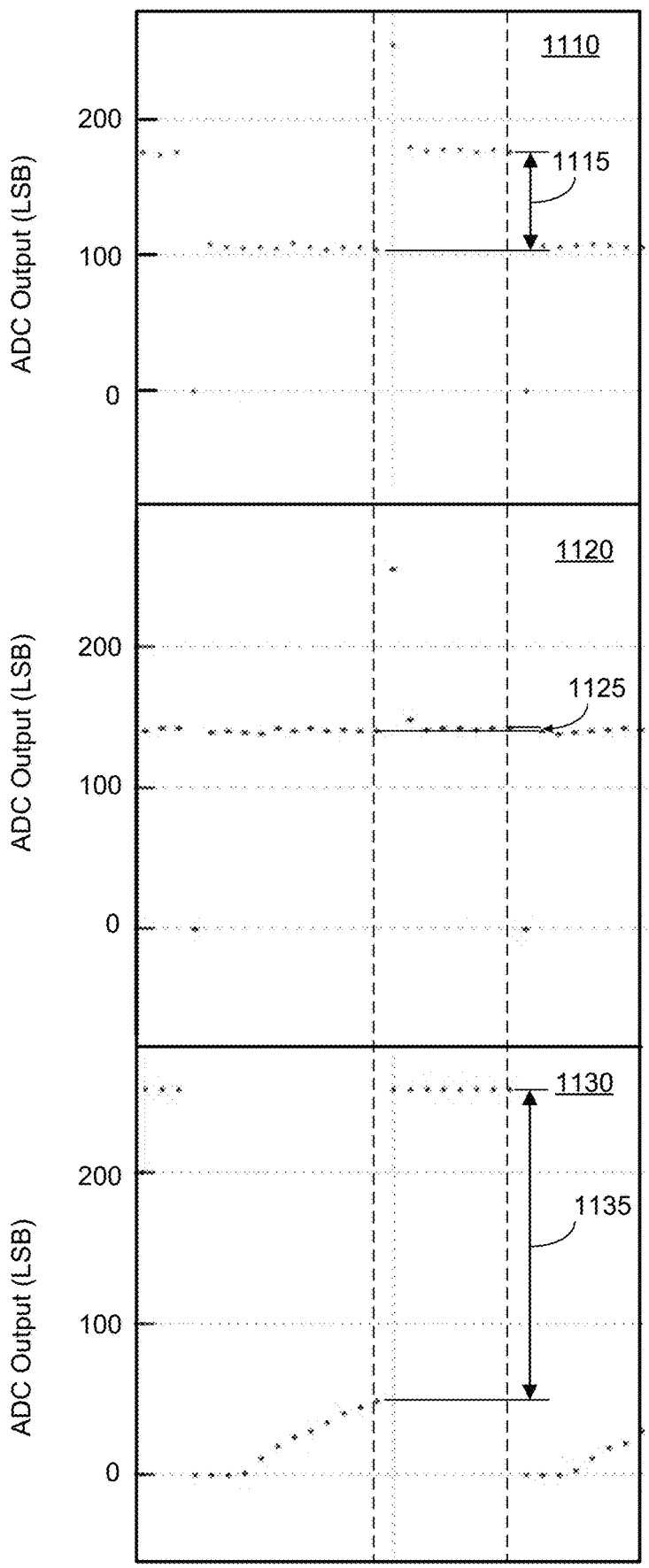
FIGS. 11A-11C show sample open channel voltage data for different states of the cell according to certain embodiments.

FIGS. 11A-11C show sample open channel voltage data for different states of the cell. FIG. 11A shows the open channel voltage data 1110 (both bright and dark periods) for a cell having a single nanopore, referred to as a single nanopore cell. FIG. 11B shows the open channel voltage data 1120 (both bright and dark periods) for a cell having zero nanopores, referred to as a zero cell bilayer. FIG. 11C shows the open channel voltage data 1130 (both bright and dark periods) for a cell having a short circuit, referred to as a short circuited cell.

According to certain embodiments, the open channel voltages obtained in step 1010 can be single point measurements or multi-point measurements. For example, a single bright channel data point (e.g., as shown in FIG. 11B) can be measured for each cell; and used to characterize the cell, i.e. whether the cell is single nanopore, zero nanopore, short, etc. A value for Vmzero may be subtracted from the data point for a given cell. For multipoint measurements, a collection of bright mode voltages can be averaged together, with Vmzero subtracted before or after the averaging. A multi-point method may involve computing difference data, e.g., point by point differences between bright and dark periods of one cycle, or point-by-point differences within a period of an AC cycle (e.g., difference between first and last points within a bright period or dark period).

FIGS. 11A-11C show a "last point delta" ("LPD") method that involves subtracting the last point of a bright period from a corresponding last point of a dark period, or vice versa. In FIG. 11A, the LPD 1115 is about 80 ADC least significant bits (LSBs) and represents the LPD of a single nanopore cell. In FIG. 11B, the LPD 1125 is very nearly 0 ADC LSB and represents the LPD of a zero nanopore cell (i.e. a cell having a bare bilayer). In FIG. 11C, the LPD 1135 is about 190 ADC LSBs and represents the LPD of a short-circuited cell, which may correspond to a cell with no membrane or multiple pores. While the precise values of the ADC LSBs for each bilayer state may vary from cell to cell as described in further detail below, FIGS. 11A-11C show that in principle the LPD can be used to discriminate between different nanopore configurations on a cell's bilayer. Thus, according to certain embodiments, as part of step 1010, the LPD of each cell is measured. As other examples, first point delta may be used or an average point delta (a difference between the average value for a bright and dark period). In other examples, the delta measurement may be made using points within the same period, in which case the measurement is referred to as a "decay delta" because the delta measures the amount of voltage decay within a cycle period, e.g., a dark decay delta may be computed by subtracting the $5^{th}$ and $10^{th}$ points of a measured during a dark period. In still yet other examples, the delta may be measured relative to a mean value that is measured outside of a normal bright or dark period, e.g., a "zero delta" may be used where the zero delta is measured between a bright period value and an offset value, e.g., a mean offset that is measured with zero volts applied across the cell In step 1020, a histogram (also referred to herein as a voltage distribution) is computed using the voltage values obtained in step 1010. The histogram may take as input, any type of measured voltages including both single point and/or multipoint measurements. For the example of the LPD described above, to compute the histogram, the full range of measured LPD values can be split into bins. For example, if the measured ADC LSBs range from 0 to 255, the data may be binned with one bin having a width of one ADC LSB, thereby having a histogram with 256 bins. Other bin widths (e.g., 2, 3, etc.) are possible without departing from the scope of the present disclosure. Once the bin width is chosen, the number of cells having that particular ADC value is counted and added to the histogram.

Figure 12:
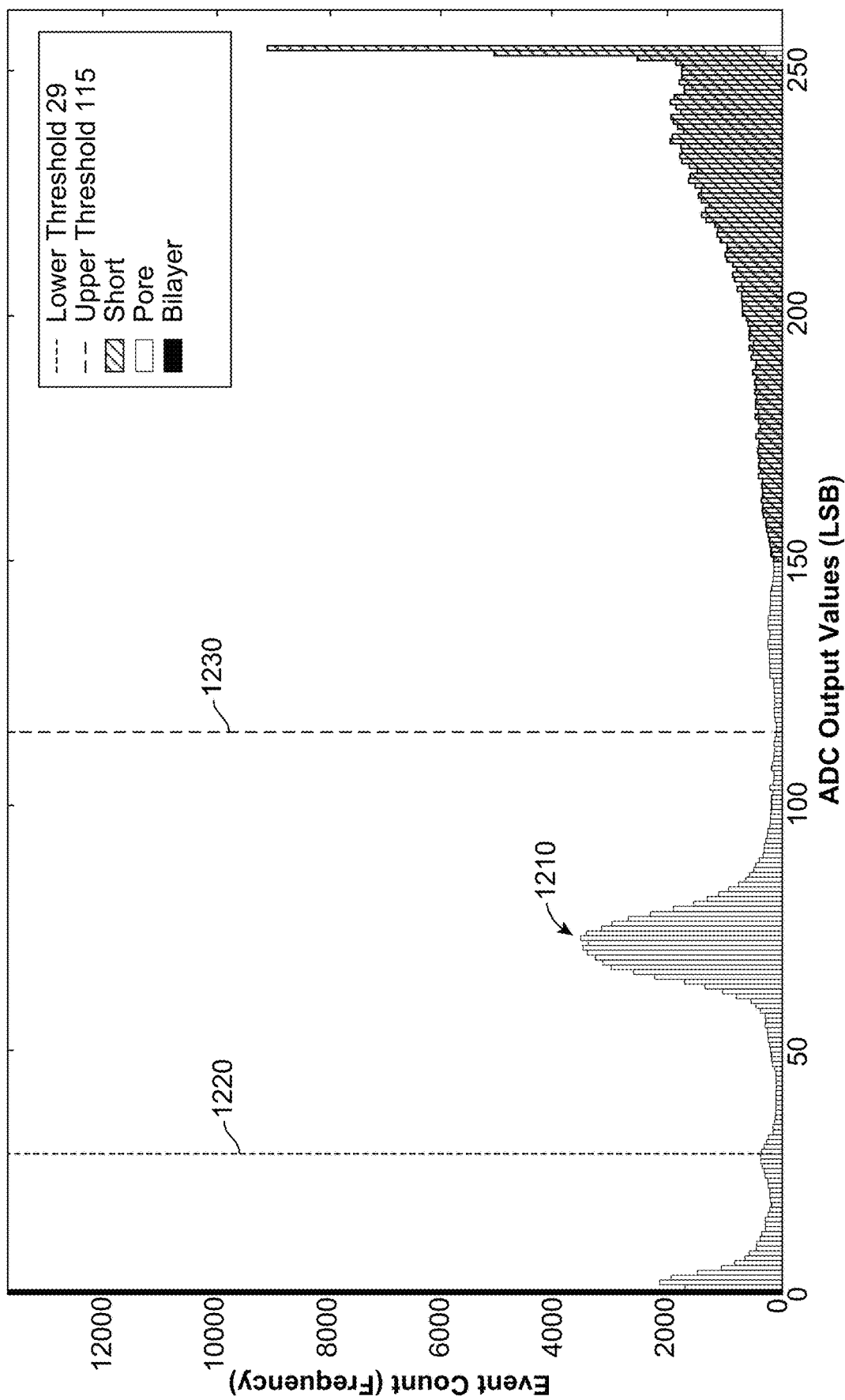
FIG. 12 shows sample histogram data according to certain embodiments.

FIG. 12 shows sample histogram data according to certain embodiments. A relatively large single nanopore peak 1210 is visible in the data. The leftmost portion of the histogram shows counts for cells having zero nanopores (low voltages) and also for cell having pseudo-pores, e.g., behavior that is similar to a pore. The rightmost portion of the histogram shows counts for cells that have more than one pore and also for cells that have short circuits (e.g., no membrane).

Referring back to FIG. 10, in step 1030, a histogram peak corresponding to cells having a single nanopore (also referred to herein as single pore cells) is identified. According to certain embodiments, neither the peak value, nor the peak width needs to be known in advance of obtaining the measured voltage data in step 1010. For example, a peak detection routine can detect boundaries and characteristics of the peaks, e.g., to identify the single nanopore peak. For instance, the center of the largest amplitude peak within a predetermined range of voltage values can be identified as the single nanopore peak. In some embodiments, the bins at or near the very end of the voltage range can be ignored during the initial peak detection routine, e.g., in FIG. 12, peak 1210 is the largest amplitude peak between bins of 2 and 250. The voltage range for identifying the peak can be established via empirical data from other sequencing chips.

In step 1040, a first set of cells located within the single nanopore peak is determined. According to certain embodiments, step 1040 can identify all cells having voltages within an identified width of the largest amplitude peak as the set of a single nanopore cells. The width parameter can be, e.g., the full width at half maximum, which can be used as a proxy for a standard deviation. In some embodiments, the width can be taken as a specified number of standard deviations, e.g., 2, 3, 4, etc. Measurements of local minima in the histogram could also be used. For example, a local minimum between the zero peak and the single nanopore peak can be used to determine a baseline for identifying the width of the single nanopore peak. Accordingly, embodiments can determine where the local maximum and minimum are within the histogram data. The integral, i.e., integrated area under histogram between the various local minimum can be used to identify the peak with the largest area, which would correspond to the single nanopore peak, under the assumption that this is the largest population for the chip as a whole.

It should be understood that the histogram peak corresponding to cells having a single nanopore need not be solely comprised of single nanopore cells to the exclusion of other types of cells. As shown in FIG. 12, the peak is not infinitely narrow and, as such, it is understood that while the population of cells within the peak will be dominated by single nanopore cells, some non-single nanopore cells may happen to have voltages that fall within the peak, depending on how the width of the peak is defined. According to certain embodiments, the width of the peak can be defined relative to the peak value, e.g., voltage cutoffs can be chosen to be where a level of the histogram is some specified fraction of a maximum value of the histogram peak (e.g., full width at half max, $1/e^2$, 119.9% level, etc.). Voltage cutoffs may be determined based on the minimum and maximum detections described above. Voltage values within the cutoffs define the set of cells that are to be considered single nanopore cells, where the number of non-single nanopore cells decreases as the width decreases. The placement of the cutoffs will involve a tradeoff between capturing a large fraction of the available single nanopore cells, while also excluding the majority of cells having something other than a single nanopore (e.g., zero nanopore cells, shorts, two or more nanopore cells, pseudo-pores cells, etc).

In the example shown in FIG. 12, cutoff 1220 is placed at 29 ADC LSBs and cutoff 1230 is placed at 115 ADC LSBs. In this example, cutoff 1220 eliminates most pseudo-pores and zero-pore cells (which have open channel voltages of less than 29 ADC LSBs), and likewise, cutoff 1230 eliminates most multi-pore and short circuited cells (which have open channel voltages of greater than 115 ADC LSBs). According to certain embodiments, to improve the accuracy of the chip, cells having voltages outside of the cutoffs may be deactivated or their outputs may be selectively removed or ignored. For example, after characterization, cells having a single nanopore may be effectively labeled by storing unique identifiers for each of these cells in memory. The during a sequencing operation, a processor may then activate only those pores that associated with a stored identifier. The converse is also possible, where cells to be deactivated are labeled with a unique identifier stored in memory.

In step 1050, a sequencing operation may be performed using only the identified single nanopore cells. The sequencing operation may proceed as described above in reference to FIGS. 3, 5, and 7.

Determining the set of single nanopore cells from a histogram (or distribution) of the measured open channel voltage data can be a robust process for identifying cells with a single nanopore because minimal assumptions may be made, as opposed to using fixed cutoff values. As the cells may vary from chip to chip and different biochemistry may be involved, such a robust process is desirable. For example, one may not know the exact value of the voltage for each single nanopore peak, and various nanopores may be used for different chips. Furthermore, the lipid bilayer can change over time. As the gain of a cell depends on both $R_{pore}$ and $C_{bilayer}$, a larger well or different solvent (or different annulus) can change gain, and therefore the open channel and threaded voltages.

IV. Sequencing Operation

Once the usable cells of a chip are identified, a production mode can be run to sequence nucleic acids, one for each usable cell. To perform sequencing, the voltage level of integrating capacitor (e.g., integrating capacitor $C_{int}$ 608 ($n_{cap}$) or capacitor $C_{bilayer}$ 626) can be sampled and converted by the ADC (e.g., ADC 610) while a tagged nucleotide is being added to the nucleic acid. The tag of the nucleotide can be pushed into the barrel of the nanopore by the electric field across the nanopore that is applied through the counter electrode and the working electrode, for example, when the applied electric field is such that $V_{liq}$ is higher than Vpre.

A. Threading

A threading event is when a tagged nucleotide is attached to the template (e.g., nucleic acid fragment), and the tag goes in and out of the barrel of the nanopore. This can happen multiple times during a threading event. When the tag is in the barrel of the nanopore, the resistance of the nanopore may be higher, and a lower current may flow through the nanopore.

During sequencing, a tag may not be in the nanopore in some AC cycles (referred to as an open-channel state), where the current is the highest because of the lower resistance of the nanopore. When a tag is attracted into the barrel of the nanopore, the nanopore is in a bright mode (or period). When the tag is pushed out of the barrel of the nanopore, the nanopore is in a dark mode (period).

B. Bright and Dark Periods

During an AC cycle, the voltage on integrating capacitor may be sampled multiple times by the ADC. For example, in one embodiment, an AC voltage signal is applied across the system at, e.g., about 100 Hz, and an acquisition rate of the ADC can be about 2000 Hz per cell. Thus, there can be about 20 data points (voltage measurements) captured per AC cycle (cycle of an AC waveform). Data points corresponding to one cycle of the AC waveform may be referred to as a set. In a set of data points for an AC cycle, there may be a subset captured when, for example, $V_{liq}$ is lower than $V_{pre}$, which may correspond to a bright mode (period) where the tag is forced into the barrel of the nanopore. Another subset may correspond to a dark mode (period) where the tag is pushed out of the barrel of the nanopore by the applied electric field when, for example, $V_{liq}$ is higher than $V_{pre}$.

C. Measured Voltages

For each data point, when the switch 601 is opened, the voltage at the integrating capacitor (e.g., integrating capacitor $C_{int}$ 608 (neap) or capacitor $C_{bilayer}$ 626) will change in a decaying manner as a result of the charging/discharging by $V_{liq}$, e.g., as an increase from $V_{pre}$ to $V_{liq}$ when $V_{liq}$ is higher than $V_{pre}$ or a decrease from $V_{pre}$ to $V_{liq}$ when $V_{liq}$ is lower than $V_{pre}$. The final voltage values may deviate from $V_{liq}$ as the working electrode charges. The rate of change of the voltage level on the integrating capacitor may be governed by the value of the resistance of the bilayer, which may include the nanopore, which may in turn include a molecule (e.g., a tag of a tagged nucleotides) in the nanopore. The voltage level can be measured at a predetermined time after switch 601 opens.

Switch 601 may operate at the rate of data acquisition. Switch 601 may be closed for a relatively short time period between two acquisitions of data, typically right after a measurement by the ADC. The switch allows multiple data points to be collected for each cycle. If switch 601 remains open, the voltage level on the integrating capacitor, and thus the output value of the ADC, would fully decay and stay there. Such multiple measurements can allow higher resolution with a fixed ADC (e.g. 8-bit to 14-bit due to the greater number of measurements, which may be averaged). The multiple measurements can also provide kinetic information about the molecule threaded into the nanopore. The timing information may allow the determination of how long a threading takes place. This can also be used in helping to determine whether multiple nucleotides that are added to the nucleic acid strand are being sequenced.

More details of the measurement circuitry and the operations of the measurement circuitry for meaning the voltage at ncap that can be used to determine the state of the nanopore cell can be found in Section II.

D. Normalization

The ADC output data captured during the sequencing can be normalized to provide greater accuracy. Normalization can account for offset effects, such as intracycle decay cycle shape, gain drift, and baseline shift. As described above, the normalization may be performed using the measured open channel voltage. For example, in some circumstances, the bright mode open channel voltage may be constant, and thus all of the bright mode data can be divided by a same normalization factor to perform the normalization.

In general, each sequencing cell has a voltage gain that depends on the lipid bi-layer capacitance. The voltage gain corresponds to the voltage difference that is achieved between the pair of electrodes (e.g., counter electrode 210 and working electrode 202). For example, given the equation of C=q/V for a capacitor, as the capacitance increases, the voltage would decrease when a same amount of charge is present. Accordingly, if the lipid bi-layer capacitance changes over time, then the voltage gain changes over time. If the voltage gain changes over time, then the bright mode and dark mode (both open channel and threaded) can change over time. In any real system, the bilayer capacitance may change over time, e.g., as the bilayer deforms. Such changes typically occur on the timescale of hundreds or thousands of seconds and, though slower than a typical threading event, still should be accounted for if high accuracy measurements are desired.

Because the voltage gain could change over time, the open channel voltage in the bright mode may not be constant over time, and thus the single value normalization described above (i.e., divide everything by a same normalization factor) may fail to normalize the entire signal over time. Instead of the constant normalization, a more complex variable normalization can be applied, e.g., the normalization can be accomplished by dividing each raw bright-mode measured ADC value with an estimate of that point's open channel value. For each non-threaded region, an estimate of the open channel voltage can be made by any number of ways, e.g., by taking a local mean value or by using more sophisticated signal processing technique such as a Kallman filter, as described in more detail below. Thus, a local estimate can be obtained for the open channel value for the bright mode, so as to normalize a data point using the estimated voltage that is local to that data point.

On the other hand, the threaded regions of the signal can provide a challenge. For some threading events, there may open channel data available if the threading rate is slow enough. When the threading rate is relatively slow, open channel values can be measured before the tag is threaded. Such open channel values can be measured for each cycle. In these cases, the limited open channel data may be used to estimate the true open channel value during the threading event. This limited open channel data (i.e., limited relative to when no threading occurs) can be used to obtain a local estimate of the open channel value (e.g., local within time, so as to account for gain drift)

However, it may be the case that the threading is fast enough that no open channel data is captured in the bright mode. When the threading rate is sufficiently fast, the tag is immediately threaded, and no open channel values are measured. This lack of open channel voltages can be problematic when trying to determine a local estimate of the open channel; if there are not open channel values for a given time interval, no local estimate can be determined for that time interval. In these cases, it is possible to determine the local estimate for the open channel data in the bright mode using the dark mode data, as described in further detail below.

Baseline shift is a phenomenon that is related to charge imbalances that build up on certain elements (e.g., $C_{dbl}$ 624) in the cell during the charging and discharging cycles that take place during the measurement process. For example, during the measurement process, excess charge can build up on the working electrode of the cell, represented by $C_{dbl}$ 624 in FIG. 6B. In one example, the charge imbalance is caused by the fact that both the nanopore and the tags have non-linear I-V characteristics. As a result of this nonlinearity, a charge and discharge cycle may not add or remove the same amount of charge to the capacitive elements. For example, negative and positive ions may not move from one electrode to the other electrode via the pore at the same rate over time, e.g., causing positive charge to build-up in the well. Note that the duty cycle can be 60% dark mode and 40% bright mode to address a typical difference in transmission rate of positive and negative ions, but when a rate changes, the duty cycle would have to change, which can be difficult to do.

As a result of this accumulated charge imbalance, the voltage measurements in a cell would increase (e.g., when positive charge builds up in the well). This shift in a baseline voltage can increase until it produces a voltage high enough to counterbalance the opposing voltage originally set up as a consequence of the charge imbalance. At which point, the charge can re-balance. Baseline shifts can occur in the both the dark mode and bright mode open channel states and in each of the four threaded states, with the magnitude and time constants for the shifts potentially being different in each of the open channel and four threaded states. As a result, the baseline shift can change in a generally random way that mirrors the stochastic binding events of the tags at the pore.

As with the gain shift phenomenon, to compensate for baseline shift, a variable, point-by-point normalization can be applied, e.g., the normalization can be accomplished by dividing each raw bright-mode measured ADC value with an estimate of that point's open channel value as described in further detail below. Such an estimate can be considered a local estimate as it is valid for a single point or a certain set of points within a time interval.

The intracycle decay is a result of capacitor $C_{dbl}$ 624 in FIG. 6B changing from one measurement to another during a cycle. This change in $C_{dbl}$ 624 affects the decay rate of the voltage at the integrating capacitor so that the decay is slower for successive measurements, thereby resulting in slight changes in the measured ADC value.

To compensate for such changes, one could take just a single voltage reading, but that may not be as accurate as a multiple measurements. Some implementations can effectively get a single measurement by taking an average (mean) of the voltages over a given cycle. Such an average can be weighted based on a calculated or expected value for the intracycle decay rate. Such an average can be used as a measured ADC value, potentially where threaded voltage in a cycle can be given the value of the average.

In some circumstances, an open channel bright voltage may not always be available. In such circumstances, an open channel dark voltage may be used. Further details regarding normalization can be found in U.S. patent application Ser. Nos. 15/632,190 and 15/628,353, which are incorporated by reference in their entirety.

E. Determining Bases

After normalization, embodiments can determine clusters of voltages for the threaded channels, where each cluster corresponds to a different tag species, and thus a different nucleotide (or base). The clusters can be used to determine probabilities of a given voltage corresponding to a given nucleotide. As another example, the clusters can be used to determine cutoff voltages for discriminating between different nucleotides (bases). In some embodiments, a histogram may be created from the normalized data, or raw data if the operation of the sequencing cell is sufficiently stable over time. Based on the histogram, a Laplacian mixture model (LMM) can then be used to determine cutoff voltages for discriminating between different nucleotides (bases). The width for the Laplacian can be determined as part of the fitting procedure. There can be 5 Laplacian functions, one for positive open channel and one for each of the four nucleotides. The clusters can be determined per cell.

In some embodiments, the sequence of nucleotide binding states and the corresponding bases may be determined using, e.g., a hidden Markov model (HMM) decoder, based on probability functions and normalized signal values. In the HMM decoder, emission probabilities corresponding to particular bases may be assigned to normalized (or non-normalized) signal values based on the histogram and/or the mixture model. For each cell state of the four cell states (A, T, C, and G), a probability function (or mixture state) can assign probabilities of being in the cell state to the different numerical values.

In some embodiments, the probability function can be determined using the plurality of counts for the bins of the histogram. Various types of probability functions can be determined, e.g., based on cutoff values, signal values corresponding to peaks in the histograms, or mixture models. Once the probability functions are determined, a probability of a particular signal value measured at a given time corresponding to a particular threading event or cell state (e.g., corresponding to C) can be determined using the probability function corresponding to that cell state. Four probabilities can be determined for each signal value, each probability function providing one probability. The cell state corresponding to the highest probability may be determined to be the cell state associated with the signal value.

Further details regarding the sequencing operation can be found in, for example, U.S. patent application Ser. No. 14/577,511 entitled "Nanopore-Based Sequencing With Varying Voltage Stimulus," U.S. patent application Ser. No. 14/971,667 entitled "Nanopore-Based Sequencing With Varying Voltage Stimulus," U.S. patent application Ser. No. 15/085,700 entitled "Non-Destructive Bilayer Monitoring Using Measurement Of Bilayer Response To Electrical Stimulus," and U.S. patent application Ser. No. 15/085,713 entitled "Electrical Enhancement Of Bilayer Formation."

V. Data Processing System

Figure 13:
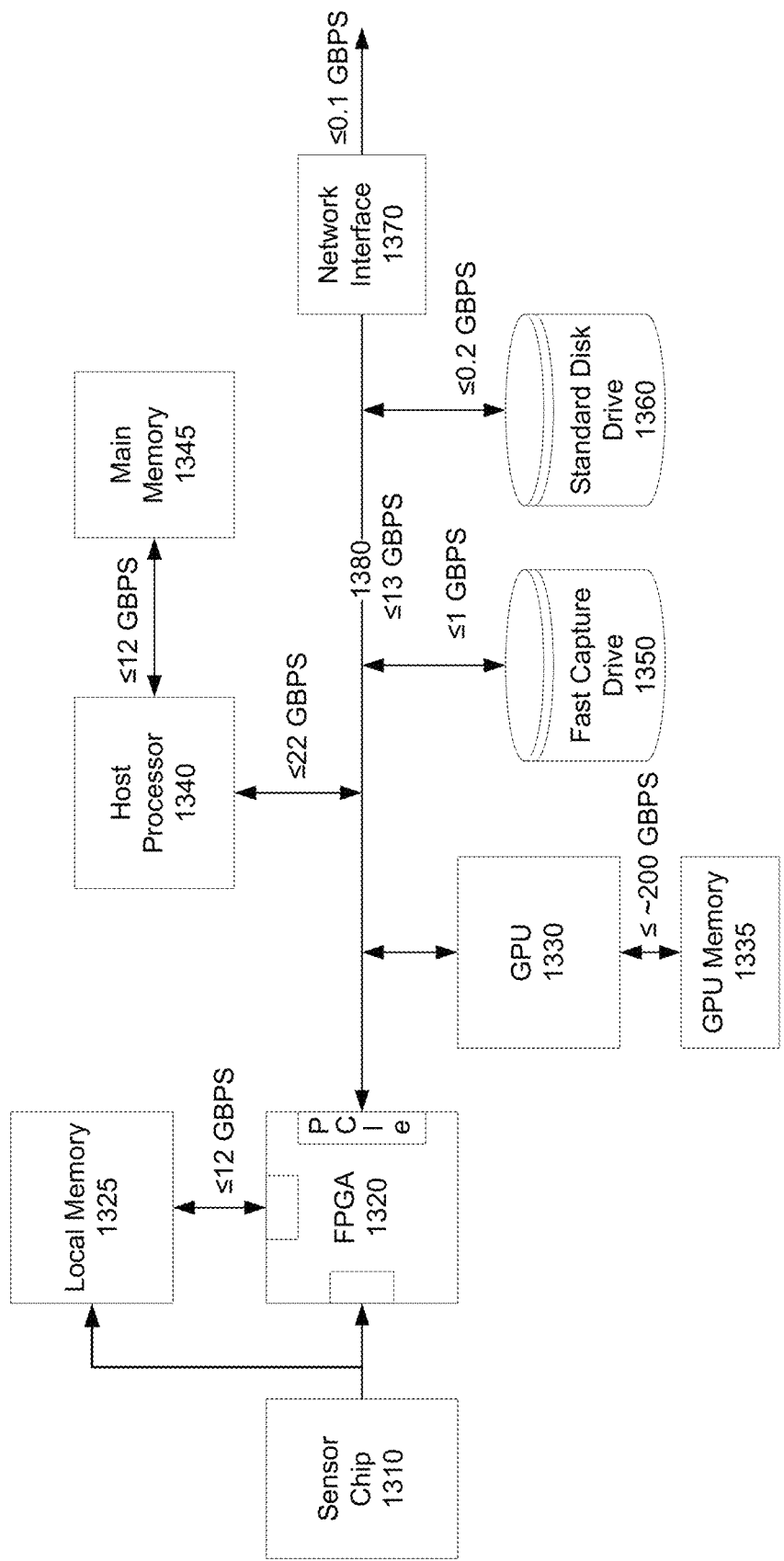
FIG. 13 illustrates a block diagram of an example system for processing data captured by an example nanopore-based sequencing chip according to certain embodiments.

FIG. 13 illustrates a block diagram of an example system for processing data captured by a nanopore-based sequencing sensor chip 1310, according to embodiments of the present invention. Sensor chip 1310 may include thousands or millions or more of cells. As described above, the data may be captured by the cells of sensor chip 1310 during various phases of cell formation and sequencing, including, for example, before the formation of the lipid layer (e.g., to check open/short of the electrical circuit), after the formation of a thick lipid layer, during the thinning of the lipid layer, after the formation of the bilayer, after the formation of the nanopore (e.g., to determine the number of nanopores for each cell or to measure open channel data for normalization), and during the sequencing of a sample (e.g., for normalization).

A sensor chip may include thousands or millions of cells, such as 100,000 or more cells, 1 million or more cells, 2 million or more cells, 4 million or more cells, or 8 million or more cells. In an example system, sensor chip 1310 may include 1 million cells, where each cell of the 1 million cells may be a nanopore-based sensor cell as described above with respect to FIGS. 1-4 and 6, and may capture, for example, ten data sample points in one cycle of an AC signal at 100 Hz. Thus, at a given time, each cell of the 1 million cells may capture one data point represented by one byte (e.g., 8 bits), and one raw data frame including 1 million bytes (MB) of data from the 1 million cells may be generated. In some implementations, the data point may be a raw data point from the ADC output (ADC value). In some implementations, rather than outputting the actual ADC values, the data point may be the difference between two consecutive raw data points from the ADC output. In some implementations, a local event detector may be used to determine whether an event has occurred at a cell and the output data point may indicate whether an event has occurred on a cell. For example, the local event detector may detect an event if a difference between a new ADC value and previous ADC value (or other reference value) is greater than a threshold hold. A data frame may indicate no event or state change on some cells and events or state changes on some other cells. Thus, a data frame comprises all of the data points across the cells at a given time. Further details regarding the data points can be found in, for example, U.S. patent application Ser. No. 14/864,400 entitled "Encoding State Change of Nanopore to Reduce Data Size."

The raw data frame may be represented by, for example, an image file that includes 8 million pixels, where the data point from each cell may be represented by the gray scale or color and/or intensity of an pixel of the image file. In each AC cycle, 10 raw data frames may be generated, one at each sample point. For example, 4 sample points may be taken in the bright period and 6 sample points may be taken in the dark period, or vice versa. Thus, in one second, 1000 (100 cycles×10 raw data frames per cycle) raw data frames may be generated, which may include 1 gigabytes (GB) (1 MB per frame×1000 frames) of data from 1 million cells. In other words, the output data rate of sensor chip 1310 may be 1 GB per second (GBPS) for a sensor chip with 1 million cells.

As shown in FIG. 13, data captured by sensor chip 1310 may be sent to an FPGA 1320 for preprocessing. FPGA 1320 may store the received data to a local memory 1325 at a data rate of, for example, 12 GBPS. Alternatively, data captured by sensor chip 1310 may be sent directly to local memory 1325. FPGA 1320 may directly send the received data through (or process the received data and then send the preprocessed data through), for example, a Peripheral Component Interconnect Express (PCIe) interface, to a PCIe bus 1380, which may have a maximum data transfer rate of, for example, 8 GBPS.

Each raw data frame only includes one data sample point from a cell, while each base is determined based on a plurality of sample data points as described above. Furthermore, a data processor may not have sufficient resources to process the raw data frames in real time. Therefore, the raw data frames may be stored first and then be processed together when raw data frames sufficient for determining a base are available. For example, data from FPGA 1320 may be stored in one or more standard disk drives 1360 or one or more fast capture drives 1350. Each standard disk drive 1360 may have a maximum write speed of 0.2 GBPS, while each fast capture drive 1350 may have a maximum write speed of 1 GBPS. Additionally or alternatively, data from FPGA 1320 may be sent to network storage devices through a network interface 1370, which may have a maximum data rate of 0.1 GBPS. Thus, to save data at, for example, 1 GBPS, multiple drives or network interfaces may be needed, which may significantly increase the cost of the system. Furthermore, the usable bandwidth of PCIe bus 1380 may be less than the full bandwidth of 8 GBPS, such as, for example, 6 GBPS (75% of the full bandwidth) due to other data transportations on the bus. Thus, in some cases, the data from FPGA 1320 may not be saved to the storage drive fast enough. A large buffer may be needed for temporarily storing the data, or some data may need to be dropped.

After the data sampling by sensor chip 1310 is complete, a graphic processing unit (GPU) 1330 or a host processor 1340 may be used to process the stored data. Host processor 1340 may include a communication interface having a maximum bandwidth of, for example, about 22 GBPS, which may not be fully utilized due to the bandwidth limitation of PCIe bus 1380. Host processor 1340 may access a main memory 1345 (e.g., a DRAM) at a maximum data rate of, for example, 12 GBPS. In various implementations, host processor 1340 may access main memory 1345 directly or through, for example, a north bridge. GPU 1330 may include hundreds or thousands of parallel processing cores, and may access a GPU memory 1335 at a maximum data rate of, for example, 200 GBPS. GPU 1330 may communicate with other components, such as standard disk drives 1360 or fast capture drives 1350, through PCIe bus 1380 at a data rate of no greater than 8 GBPS, such as about 1 GBPS. GPU 1330 may be more suitable for parallel processing data from the thousands or millions of cells of sensor chip 1310.

To process the stored data, GPU 1330 may need to read the data back from the storage device, and the data processing speed may be limited by the speed of the data read-back. Thus, if sensor chip 1310 is used to sample data, for example, for 2 hours or more for an assay, 2 hours or more may be needed to read the stored data back. Thus, the data processing time may be very long.

Therefore, to reduce the cost of the data processing system and improve the data processing efficiency of the system, it may be desirable to process the data captured by sensor chip 1310 in real time and reduce the amount of data transfer between different functional blocks of the system.

VI. Data Frames and Frame Maps

Figure 14:
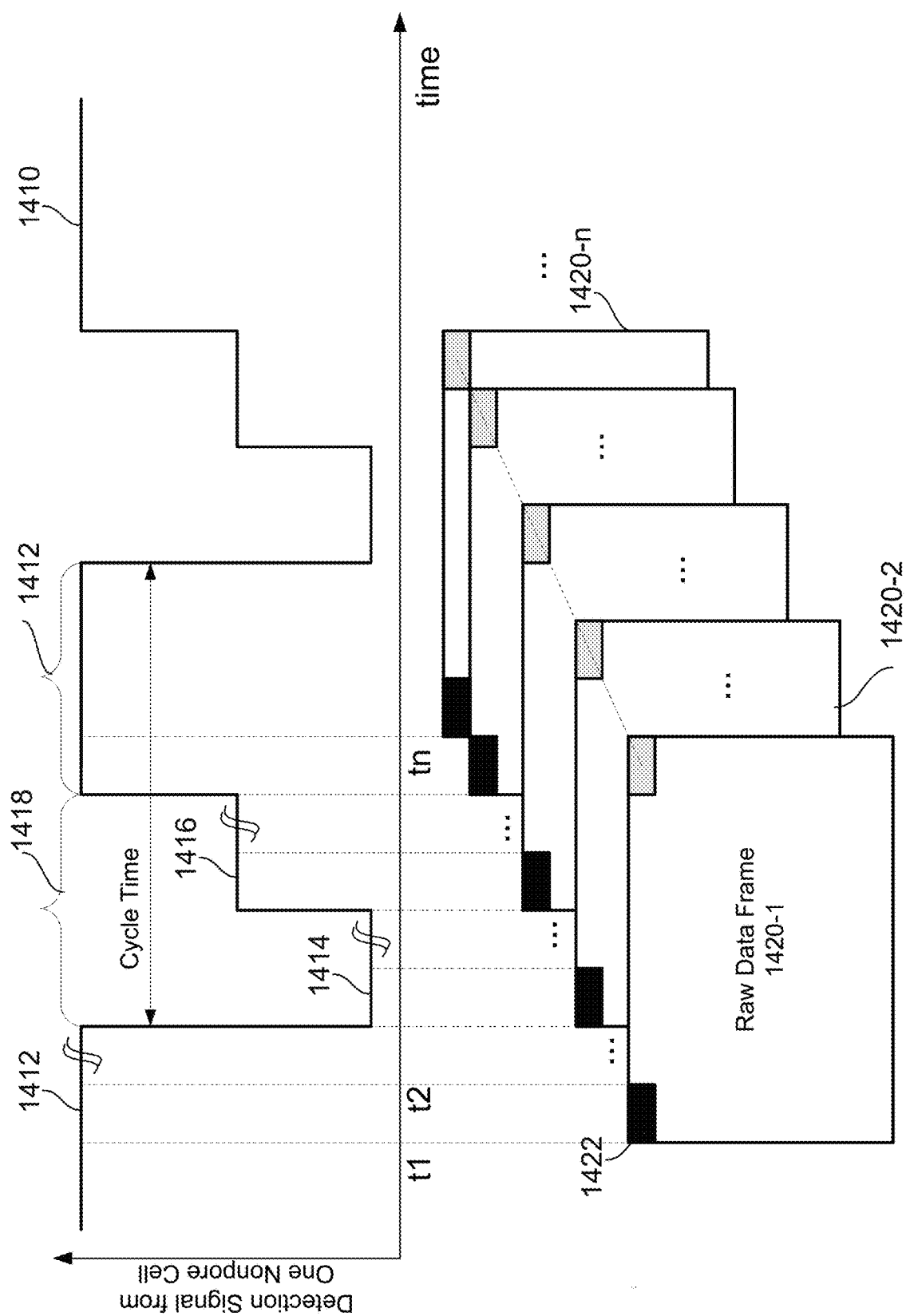
FIG. 14 illustrates examples of raw data frames captured by an example nanopore-based sequencing chip according to certain embodiments.

FIG. 14 illustrates examples of raw data frames captured by an example nanopore-based sequencing chip, such as sensor chip 1310 of FIG. 13, according to some embodiments of the present invention. As shown in FIG. 14, a detection signal from a first nanopore cell may be illustrated by a waveform 1410. Waveform 1410 may include a plurality of AC cycles, and each AC cycle may include a dark period 1412 and a bright period 1418 as described above with respect to FIG. 7. As shown, the signals at 1412 and 1414 are open channels values when no tags are in the nanopore, e.g., no threading. Bright period 1418 may include an insertion period 1416, during which the value of the detection signal may be different as a result of a tag being threaded into the nanopore during this time. Although FIG. 14 shows that the detection signal at dark period 1412 is higher than the detection signal at bright period 1418, the detection signal at the dark period may be lower than the detection signal at the bright period, depending on how the cell voltage reference (e.g., voltage source $V_{pre}$ 605) is configured.

In each AC cycle, multiple data samples, such as, 8, 10, 16, or 24 samples, may be captured by each nanopore cell. Some data samples, for example, the ones captured during a dark period by a nanopore cell, may be the same or roughly similar. The data in FIG. 14 is idealized in that the lines are perfectly flat. As mentioned above, measurements (e.g., voltage or current) may be made multiple times during the bright and dark period. The value at each time might vary slightly, e.g., depending on the resolution of the measurement; an ADC output could have a range of 256 values, and thus different ADC output values of an open channel can vary within a few ADC least significant bits (LSBs) of each other.

As shown in FIG. 14, at time t1, each cell of the sequencing chip may capture one sample, for example, from ADC 610 of FIG. 6. For example, the first nanopore cell may capture one sample 1422, which can comprise a single ADC value. The samples captured by the nanopore cells in the sequencing chip may form a raw data frame 1420-1. Similarly, at time t2, each cell of the sequencing chip may capture one sample and the samples captured by the nanopore cells in the sequencing chip may form a raw data frame 1420-2, and so on. At time tn, each cell of the sequencing chip may capture one sample and the samples captured by the nanopore cells in the sequencing chip may form a raw data frame 1420-n.

During various phases of the cell formation, cell calibration, and sequencing, different raw data frames may be generated. In some embodiments, the different raw data frames may include different parameters associated with the cells. The raw data frames to be generated may be dynamically selected or adjusted by changing, for example, the waveforms (e.g., the time, level, and shape) of the ADC reference signals, the waveforms of the signals applied to the working electrode and/or the counter electrode, and the like.

A. Dropping Frames

To reduce the amount of data to be transferred and stored, a preprocessor, such as FPGA 1320 of FIG. 13, may drop some frames. For example, rather than sending all 10 raw data frames (e.g., 6 for the bright period and 4 for the dark period) in an AC cycle, 7 raw data frames in the AC cycle may be dropped, and the remaining 3 raw data frames may be sent. In one implementation, the 3 raw data frames may include one captured during the dark period and two captured during the bright period (including one captured during the insertion period). As such, the amount of data to be transferred may be reduced to about 30% of the raw data captured by the sequencing chip.

In various embodiments, the number of frames to be dropped and the location of the frames to be dropped may be different. For example, in some embodiments, a first frame in a dark period may be kept and the other frames in the dark period may be dropped. In some embodiments, a frame in the middle of a dark period may be kept and the other frames in the dark period may be dropped. In some embodiments, the last frame in a dark period may be kept and the other frames in the dark period may be dropped. In some embodiments, two or more frames in the dark period may be kept and the other frames in the dark period may be dropped, where the two or more frames may include at least one of a first frame, a middle frame, or a last frame in the dark period. The frames in the bright period or the insertion period within the bright period may be handled similarly. In some cases, no data frame from every Nth cycle (e.g., every tenth cycle) is dropped, where the data frames in the every Nth cycle may be used for normalization or calibration purposes.

As described in detail below, a frame map may be used to identify the corresponding raw data frames. For example, the frame map may specify 2 bright raw data frames and one dark raw data frame in a cycle. The reduced set of raw data frames may then be processed by a processor based on the frame map.

Even though the above described method may reduce the amount of data being transferred and stored, it may lose useful information when simply dropping some raw data frames, for example, if the waveform of the detection signal of a nanopore cell is unpredictable or irregular in at least some cycles. It may be desirable to reduce the amount of data transfer and storage without losing some useful information in the data samples captured by the nanopore-based sequencing chip.

B. Pre-Processing

According to certain aspects of the present disclosure, a preprocessor (e.g., FPGA 1320) may process raw data captured by the nanopore-based sequencing chip (e.g., sensor chip 1310) to extract various relevant information, and send the relevant information to a processor (e.g., GPU 1330) for determining bases in the nucleic acid molecule to be sequenced in real time.

In some examples, the preprocessor may extract relevant information for determining bases from the raw data frames and generate digested data frames that include the extracted information, where the number of digested data frames is significantly lower than the number of raw data frames. For example, 1000 raw data frames (100 cycles×10 raw data frames per cycle) may be generated in one second, which may result in 8 GB of data (i.e., 8 GBPS). The raw data frames may be sent directly to a buffer, such as local memory 1325, which may temporarily store the raw data frames until there is sufficient information in the data frames for a processor (e.g., GPU 1330) to identify one or more bases. The number of raw data frames needed to identify one or more bases may depend on the kinetics of the sequencing process. For example, in examples where one or two bases may be identified in a second, the buffer may store 1000 raw data frames (e.g., 8 GB) captured by the nanopore-based sequencing chip. The buffer may be, for example, 16 GB or larger, such that 8 GB may be used to receive new data and the other 8 GB may be used to store previously captured data that is being processed by the preprocessor.

In some embodiments, the preprocessor may compare consecutive frames, drop most data frames that are substantially similar, and only keep a representative frame for the similar frames, as described above. For example, the preprocessor may keep the first frame in the dark period, the first frame in the bring period, and the first frame in the insertion period, and drop subsequent frames in each of the dark period, the bright period, and the insertion period that are similar to the first frame in the corresponding period. In some embodiments, the preprocessor may generate a digested data frame that is the average of the data frames in the dark period, the bright period, or the insertion period. In some embodiments, the preprocessor may generate a digested data frame that includes the median value of the data in the data frames in the dark period, the bright period, or the insertion period for each cell. In this way, the number of digested data frames may be reduced to, for example, about 30% of the number of raw data frames.

In some embodiments, the preprocessor may determine events from the raw data frames. For example, the preprocessor may determine a difference (or first order derivative) between data in two consecutive raw data frames for a cell, and if the difference is greater than a threshold value, an event may be detected. Based on the polarity and/or amplitude of the data change, it may be determined, for example, whether a threading event has occurred. A digested data frame that includes the information of the detected event may be generated and sent to the processor for determining the bases, while the raw data frames may be dropped. Other examples of digested data frames may be generated from the raw data frames as described in detail below.

Thus, in some cycles, multiple digested data frames may be generated in each cycle, while in some cycles, one digested data frame (e.g., a frame including event information) may be generated across multiple cycles. In this way, the data frames sent to the rest of the data processing system may be reduced significantly, and thus the rest of the data processing system may not need high bandwidth data communication. For example, the processor may be able to receive and process the digested data frame in real-time, and may only need to send the determined bases in the DNA molecules to a local storage device, such as standard disk drive 1360 or fast capture drive 1350, or network storage devices, through, for example, network interface 1370. As an example, if the nanopore-based sequencing chip includes 8 million nanopore cells, and each nanopore cell may be used to identify two bases per second, 16 million bases may be identified in one second. If the information of each base is represented by, for example, 4 bytes, the data to be stored in the storage device is 64 MB in one second. Thus, a bandwidth of only 64 MBPS may be used to write data into the storage device. A single standard disk drive, such as standard disk drive 1360, may be sufficient for storing the information of the identified bases.

The preprocessor may extract various information from the captured data. For example, in some cases, the preprocessor may extract a first point delta that corresponds to a difference between the data of the first frame and another frame in a cycle from the detection signal of each nanopore cell, and generate a digested data frame F that includes the first point delta in the cycle for each of the nanopore cells. A frame F may be generated every a few cycles and may be used during bilayer formation (one example phase of operation). For example, a first point delta value can be proportional to the capacitance of the bilayer, which is proportional to the thickness of the bilayer. The digested frame map can thus be used to determine whether a desirable thickness of the bilayer has been achieved.

Such a frame F may be used less often or not at all in other phases of operation, e.g., after bilayer formation. Accordingly, some digested frames may only be used during certain phases of operation. Different frame maps can be provided to the preprocessor during different phases so as to control the operation of the preprocessor during a particular phase.

In some cases, the preprocessor may extract the last point delta that corresponds to a difference between the data of two frames in a cycle from the detection signal of each nanopore cell, and generate a digested data frame L that includes the last point delta in the cycle for each of the nanopore cells. A frame L may be generated every a few cycles and may be used during bilayer formation.

In some cases, the preprocessor may extract the median data point in a cycle from the detection signal of each nanopore cell, and generate a digested data frame M that includes the median data point in the cycle for each of the operational nanopore cells. A frame M may be generated in every cycle and used in, for example, Kalman filtering for sequencing.

In some cases, the preprocessor may extract information regarding the decay of the detection signal in one or more cycles from the detection signal of each nanopore cell, and generate a digested data frame D that includes the decay information in the one or more cycles for each of the nanopore cells. The decay information may include the difference between two frames within a period, and may indicate how a waveform of ADC values changes during the period. A frame D may be generated every a few cycles, for example, during a dark period, and may be used during bilayer formation and during sequencing. For example, a frame D in the dark period may be used to identify nanopores. In some embodiments, the decay information may include a rate of change of the waveform of ADC values.

In some cases, the preprocessor may extract event information of the detection signal in one or more cycles from the detection signal of each nanopore cell, and generate a digested data frame E that includes the event information in the one or more cycles for all nanopore cells. An event may be detected when, for example, there is a jump in the detection signal caused by, for example, a tag insertion or a tag deletion during a bright period. For example, the event information may indicate whether a threading event has occurred. In some embodiments, the frame E may include "true" or "false" indication (e.g., "0" or "1") of whether an event has occurred. For example, if the ADC values from a cell change more than a certain percent from one frame to the next, a threading event may occur, and the frame E may include a "true" or "1" for the cell. Cells that do not detected an event may have corresponding values of "false" or "0" in the frame.

In some cases, the preprocessor may extract timing information, such as certain length of time or the time when an event occurs, in one or more cycles from the detection signal of each nanopore cell, and generate a time frame. A time frame may include timing information of event(s) detected in the cells. For example, if an event for cell happens between frames 6 and 7 in a cycle with 10 bright frames, then value for the cell in the time frame may be 6. In some implementations, a time frame may not be generated, and a processor may extract the timing information based on timing information in the header of other frames.

The above examples are for illustration purposes only, and a person skilled in the art will appreciate that there may be other specialty information that may be extracted by the preprocessor and included in a digested data frame.

In some embodiments, each digested data frame may include a header that may include a timestamp for the digested data frame, a type of the digested data frame, or other information regarding the digested data frame. In some cases, multiple digested data frames may be generated in a cycle. For example, a first point data frame F, a median data point frame M, and a decay frame D may be generated in one cycle. In some cases, no digested data frame may be generated in a cycle. In some cases, one digested data frame may be generated in multiple cycles.

C. Frame Map

As described above, in various embodiments, a frame map may be used to identify the corresponding digested data frames and/or raw data frames and sent to the processor by the preprocessor, such that the processor may know what data frames it has received and determine bases using the data frames accordingly. For example, in some embodiments, a frame map may be generated for each cycle, where the frame map may include information regarding the frames included in each cycle. In some embodiments, a frame map may be generated for multiple cycles, where the frame map may include information regarding frames generated across the multiple cycles. In some embodiments, a frame map may be generated, for example, every 100 cycles, every 1 second, or for raw data frames that include sufficient information for determining a base.

In some examples, the frame map may be predetermined by a user or operator of the sequencing system. In some examples, the frame map may be determined by the preprocessor dynamically. In some examples, the frame map may be determined by a processor, which may send the frame map to the preprocessor to request data frames identified in the frame map.

D. Example Results

Figure 15:
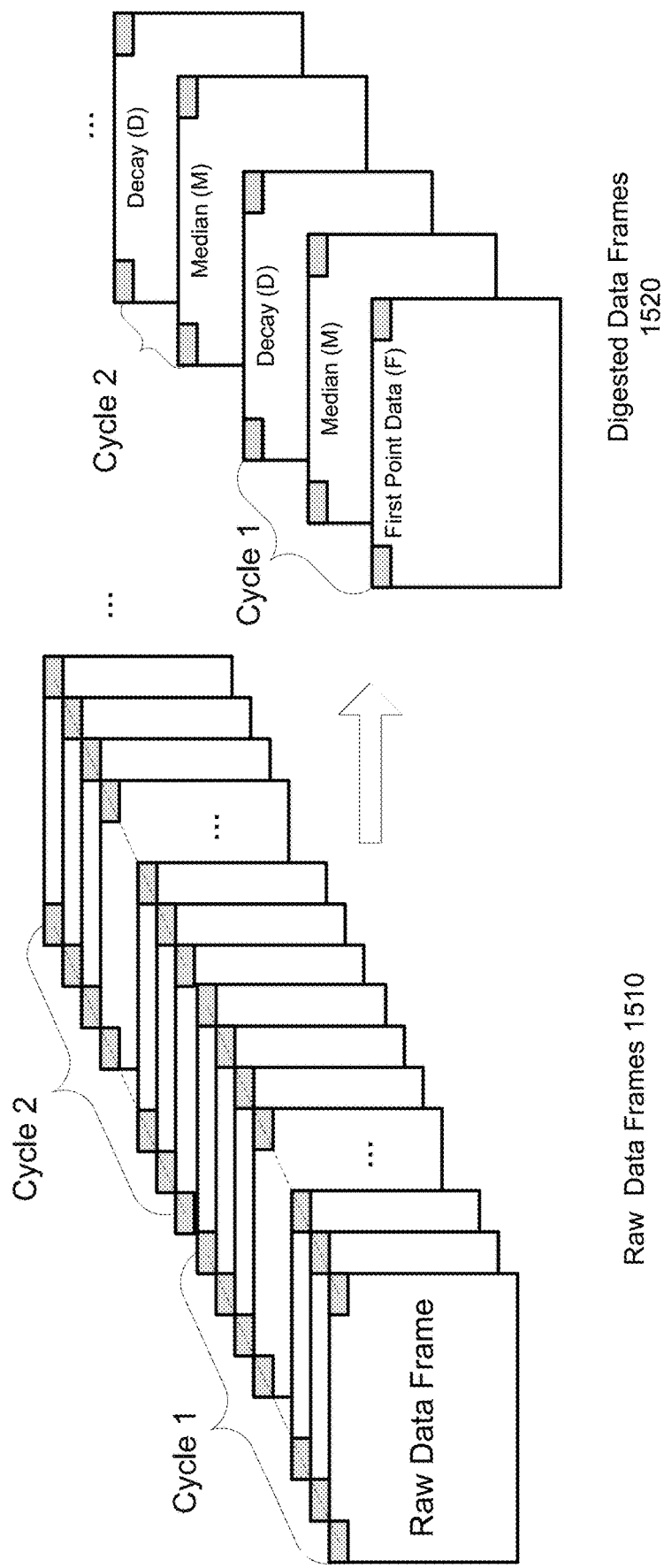
FIG. 15 illustrates example digested data frames generated by preprocessing raw data frames captured by an example nanopore-based sequencing chip according to certain embodiments.

FIG. 15 illustrates example digested data frames generated by preprocessing raw data frames captured by an example nanopore-based sequencing chip, according to some embodiments of the present invention. As shown in FIG. 15, a plurality of raw data frames 1510 captured in a sequencing assay may be preprocessed and converted into a much smaller number of digested data frames 1520. Digested data frames 1520 may then be sent, together with a frame map identifying the types of digested data frames in one or more cycles, to a processor with multiple cores, such as a GPU, for real-time parallel processing to identify bases in the nucleic acid molecule. For example, as shown in FIG. 15, the raw data frames in cycles 1 may be preprocessed and converted to three digested data frames, including a first point data frame F, a median data point frame M, and a decay information frame D, rather than, for example, 15 or more raw data frames as described above.

In cycle 2, the 15 or more raw data frames may be processed and converted to two digested data frames, which may include a median data point frame M and a decay information frame D. As described above, in some cases, some raw data frames (e.g., all raw data frames in every Nth cycle) may be sent by the preprocessor to a processor, for example, for normalization or calibration purposes. A frame map that identifies the converted digested data frames may also be generated and sent to the processor. The information in the frame map may then be used by the processor to determine the bases based on the digested data frames.

Figure 16:
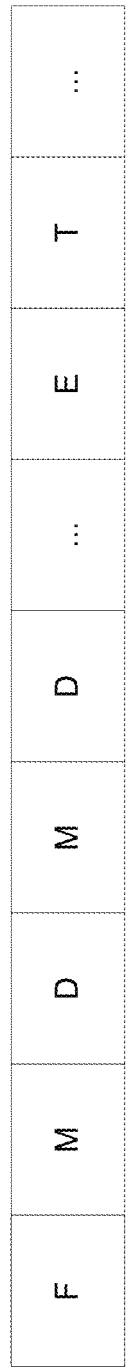
FIG. 16 illustrates an example frame map according to certain embodiments.

FIG. 16 illustrates an example frame map 1600 generated for the example shown in FIG. 15. As shown in FIG. 16, frame map 1600 identifies a list of digested data frames sent to the processor in a sequence. For example, the first digested data frame is a first point data frame F, followed by a median data point frame M and a decay information frame D, which are generated from the raw data frames in cycle 1 shown in FIG. 15. Frame map 1600 also identifies a median data point frame M and a decay information frame D generated from the raw data frames in cycle 2 shown in FIG. 15. Frame map 1600 may also identify that one of the digested data frame is an event frame E and the next digested data frames is a time frame T that includes time information of the events identified in frame E.

As another example, an example frame map may be described as ×10{2MD}×1{RMD} for every 16 cycles. The example frame map may indicate 3 frames (a frame M for the bright period, a frame M for the dark period, and a frame D in the dark period) in each of the first 15 cycles and 3 frames (a frame R (e.g., the first raw frame), a frame M, and a frame D) in every eleventh cycle.

Even though the examples shown above with respect to FIGS. 14-16 are for compressing data collected during a sequencing period, one skilled in the art would understand that the techniques can be used to compress the output data from the sensor chip during or after the formation of the sensor cells as described above in Section III. For example, data points can be measured by a sensor cell before the formation of the lipid layer (e.g., to check open/short of the electrical circuit), during the formation of the bilayer (e.g., the thinning of the lipid layer), after the formation of the bilayer, after the formation of the nanopore (e.g., to determine the number of nanopores for each cell or to measure open channel data for normalization), and during the sequencing of a sample (e.g., for normalization). These data points may be sent to the preprocessor in a set of raw data frames. The raw data frames may then be compressed or filtered by the preprocessor to generate the digested data frames that may be used to determine the state of the cell at different phases of the cell formation and sequencing process, such that only the digested data frames may be sent to a processor (e.g., GPU 1330) for determining the state of the cell. Other data points that may not be used to determine the state of the cell may not need to be forwarded to the processor.

In one example, during the dry check, the preprocessor may take the difference between two data points (included in two different raw data frames) from each cell to generate a digested data frame that includes the WPD (or any of SPD, LPD, FPD, and XPD) for each cell. In another example, during the dry check, the preprocessor may take the difference between two data points from each cell to generate a digested data frame that includes the SPD (or any of WPD, LPD, FPD, and XPD) for each cell. In yet another example, during the electroporation, the preprocessor may take the difference between two data points from each cell to generate a digested data frame that includes the DDD (or LPD) for each cell. The digested data frame may be used to determine a state of the cell.

At various phases during the cell formation and sequencing process, the state to be determined for each cell may include, for example, an open state or a short state during the dry or wet check phase, the presence or absence of a bilayer in the cell, the presence or absence of a nanopore in the cell, or the base (A, T, C, or G) whose associated tag is being threaded through the nanopore of the cell. A person skilled in the art would understand that many different alternative digested data frames and any combination of different digested data frames can be generated as needed for determining the states of the cells at different phases during the cell formation and sequencing process.

VII. Example Method

FIG. 17 is a flow chart 1700 illustrating an example method of operating a sequencing system configured to sequence a plurality of (e.g., 100,000 or more) DNA molecules in parallel according to certain embodiments. The method may be performed by a preprocessor, such as FPGA 1320 of FIG. 13.

At block 1710, a preprocessor (e.g., FPGA 1320) of the sequencing system may receive a set of data frames from a sensor chip including a plurality of cells. Each cell of the plurality of cells may be configured to generate detection signals for determining a state of the cell over time. Each data frame of the set of data frames may include detection signals from the plurality of cells and correspond to a different time. In some embodiments, the set of data frames may include data frames that are generated during a formation of the plurality of cells. In some embodiments, the set of data frames may include data frames that are generated during a calibration or a sequencing cycle of the plurality of cells. The state of a cell may include, for example, an open state or a short state of the cell, the presence or absence of a bilayer in the cell, the presence or absence of a nanopore in the cell, a base associated with the cell, or any combination thereof.

At block 1720, the preprocessor may extract information from the detection signals of the plurality of cells in the set of data frames to obtain digested information. The digested information may be used in determining the states of the plurality of cells. In some embodiments, the digested information may include a difference between the first data point in the bright period of an AC signal cycle and a first data point in the dark period of the AC signal cycle (i.e., FPD) for each of the plurality of cells. In some embodiments, the digested information may include a difference between the last data point in the bright period of an AC signal cycle and the last data point in the dark period of the AC signal cycle for each of the plurality of cells (i.e., LPD). In some embodiments, the digested information may include a difference between the last data point in a bright period and the first data point in the next dark period (i.e., SPD pos/neg) for each of the plurality of cells. In some embodiments, the digested information may include a difference between the last data point in a dark period and the first data point in the next bright period (i.e., SPD neg/pos) for each of the plurality of cells. In some embodiments, the digested information may include a difference between two data points in a dark period of an AC signal cycle (i.e., DDD) for each of the plurality of cells.

At block 1730, the preprocessor may generate a group of digested frames that includes the digested information extracted from the set of data frames. The number of digested frames in the group of digested frames may be less than the number of data frames in the set of data frames. In some embodiments, the group of digested frames may include one or more data frames from the set of data frames. In some embodiments, the preprocessor may also generate a frame map that identifies characteristics of the group of digested frames. In some embodiments, the frame map may identify digested frames generated for one or more sequencing cycles.

At block 1740, the preprocessor may send the group of one or more digested frames, and/or the frame map to a processor for use in determining the states of the plurality of cells.

Even though FIG. 17 describes the operations as a sequential process, many of the operations can be performed in parallel or concurrently. In addition, the order of the operations may be rearranged. An operation may have additional steps not included in the figure. Some operations may be optional, and thus may be omitted in various embodiments. Some operations described in one block may be performed together with operations at another block. For example, some operations may be performed in parallel. Furthermore, embodiments of the methods may be implemented in hardware, software, firmware, middleware, microcode, hardware description languages, or any combination thereof.

VIII. Adaptive Data Preprocessing/Conversion

As described above, a preprocessor of a data processing system may convert raw data frames to digested data frames to significantly reduce the amount of data to be sent through various buses in the system. The reduction of the amount of data can allow further processing in real-time, thereby enabling determining bases in the nucleic acid molecule under test in real time. Thus, the system may have extra bandwidth and/or processing power at least at some time.

In some cases, the system may determine that a better accuracy and thus more information from the captured data may be needed. The system may provide feedbacks or the status of various components of the system to the preprocessor such that the preprocessor can change its operation based on the feedbacks and/or the status of various components of the system. For example, assume that the tag insertion is slow, and the system is using a frame map that includes one raw frame for each cycle, which includes 4 raw frames during the bright period and 6 raw frames during the dark period (i.e., 10 raw frames per cycle). Other 9 raw frames may be ignored or dropped. If the system determines that the tag dwell time is short, which may occur because, for example, the insertion rate of the polymerase has been increased, the system may change the frame map to include more than one raw frame (e.g., 3 or more) of the 10 raw frames in each cycle (i.e., fewer raw frames may be dropped) such that it may detect the tags with a better accuracy. In some embodiments, the system may change the frame map to include, for example, more than 10 raw frames per cycle, such that more raw frames may be generated and kept (rather than dropped) in each cycle. The dwell time may depend on the biochemistry process. For example, for a system that can be used to identify one base per second and has a threshold for dwell of 10%, the dwell time would be between 100 ms and 1 second.

In some embodiments, the preprocessor may be programmed dynamically based on, for example, available bandwidth, the quality of the received data, or desired accuracy, to change the way that the raw data frames are processed and the data frames to be sent to a processor, such as GPU 1330 of FIG. 13, for determining bases in the sample under test. For example, if the processor detects very few events, such as threading event, it may send a request to the preprocessor to ask for more data that includes more digested data frames and/or raw data frames. For example, if the preprocessor was only sending two or three data frames per cycle before, the preprocessor may be requested to send four frames, six frames, or more frames in each cycle, which may include digested data frames, raw data frames, or any combination of digested data frames and raw data frames. The preprocessor may be requested to send, for example, four data points in the bright period and two data points in the dark period of a cycle. In some cases, the system may determine that the rate of determining bases in a sample goes down, and may request more data from the preprocessor. In come case, the processor may determine that it has extra capacity and may be able to take more data, and may request the preprocessor to send more data for a better accuracy.

In some cases, when the processor or other components of the system determine that data is provided at a rate that the processor or other components of the system do not have enough capacity to handle, the processor or other component of the system may send a request to the preprocessor to reduce the amount of data sent out by the preprocessor, with the expectation that a higher error rate may be resulted and the quality of the sequencing may be reduced.

Figure 18:
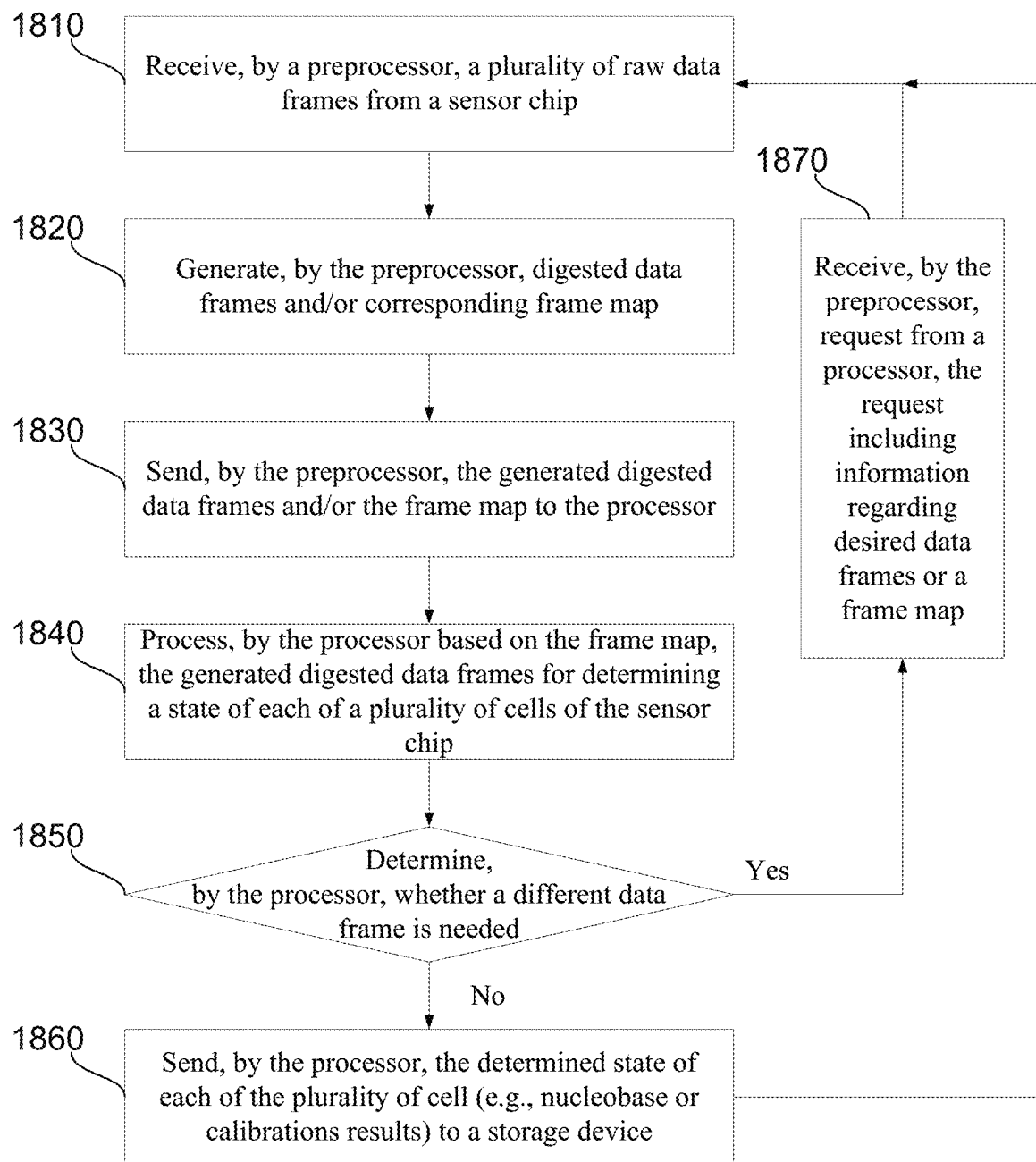
FIG. 18 is a flow chart illustrating an example method of adaptive data processing according to certain embodiments.

FIG. 18 is a flow chart 1800 illustrating an example method of adaptive data processing, according to some embodiments of this invention. The adaptive data processing may occur at different phases during or after the formation of sensor cells as described above. At block 1810, a preprocessor, such as FPGA 1320 of FIG. 13, may receive a plurality of raw data frames from a sensor chip, such as sensor chip 1310. In some embodiments, the plurality of raw data frames may include sufficient information to determine one or more bases. For example, the plurality of raw data frames may include raw data frames received in every second, such as, for example, 1000 raw data frames. In some embodiments, the plurality of raw data frames may include sufficient information to determine an open or short state of the cell, a presence or absence of a bilayer in the cell, a presence or absence of a nanopore in the cell, or a base associated with the cell during a time period.

At block 1820, the preprocessor may generate digested data frames and/or the corresponding frame map based on the plurality of raw data frames received, as described above. The digested data frames to be generated may be determined by a user or operator of the system, by the preprocessor dynamically based on the raw data frame received, or by a processor (e.g., GPU 1330 or host processor 1340 of FIG. 13) that determines bases using the digested data frames, where the processor may send a request to the preprocessor to request specific types of data frames. Examples of the digested data frames may include a digested data frame including the FDP, LDP, SPD, WPD, DDD, railed value, median data point (e.g., in a median data point frame M), decay information (e.g., in a decay information frame D), first point data (e.g., in a first point data frame F), or event information (e.g., in an event frame E) for each cell, as described above.

At block 1830, the preprocessor may send the generated digested data frames and/or the corresponding frame map to the processor via a bus, such as a PCIe bus. The bus may have sufficient bandwidth for transporting the digested data frames, such as no less than 1 GBPS, 2 GBPS, 4 GBPS, or 8 GBPS.

At block 1840, the processor may process the received digested data frames to determine the states of the cells, for example, using the frame map. The processor may include, for example, $1\times10^3$, $1\times10^4$, $1\times10^5$ or more processing cores that can process digested data associated with $1\times10^3$, $1\times10^4$, $1\times10^5$ or more sensor cells in parallel. For example, as described above, the bases whose associated tags are threaded and repelled through the nanopores in the cells during the sequencing may be determined, for example, based on the measured voltage levels and the cut-off voltage levels for distinguishing different tags complexed with different polymerases. Other states, such as an open state or a short state during the dry or wet check phase, the presence or absence of a bilayer in the cell, or the presence or absence of a nanopore in the cell, may also be determined using the digested data frame(s) generated from raw data frames captured during different phases of the cell formation process.

At block 1850, the processor may determine whether a different data frame is needed. For example, as described above, the processor may determine, based on the results of the processing at block 1840, whether more or less data frames are needed and/or what data frames are needed. In some embodiments, the processor may determine a desired frame map.

At block 1860, if the processor determines that the received data frames are appropriate and no change to the way that the preprocessor generates digested data frames may be needed, the processor may send information regarding the determined bases to a storage device, such as a disk drive.

At block 1870, if the processor determines that different data frames may be needed, the processor may send a request to the preprocessor, where the request may include information regarding desired data frames or a desired frame map. For example, the request may ask for more or less data frames, identify specific data frames to be generated, or include a desired frame map.

After block 1860 or 1870, the process may continue to receive raw data frames and preprocess the received raw data frames to generate digested data frames, based on the request (if any). It is noted that even though FIG. 18 describes the data processing as a sequential process, many of the operations can be performed in parallel or concurrently. In addition, the order of the operations may be rearranged. An operation may have additional steps not included in the figure. Some operations may be optional, and thus may be omitted in various embodiments. Some operations described in one block may be performed together with operations at another block. For example, some operations may be performed in parallel. Furthermore, embodiments of the methods may be implemented in hardware, software, firmware, middleware, microcode, hardware description languages, or any combination thereof.

IX. Computer System

Any of the computer systems mentioned herein may utilize any suitable number of subsystems. Examples of such subsystems are shown in FIG. 19 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 19 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated.

All patents, patent applications, publications, and descriptions mentioned herein are incorporated by reference in their entirety for all purposes. None is admitted to be prior art.

What is claimed is:

1. A method of operating a sequencing system configured to sequence at least 100,000 DNA molecules in parallel, the method comprising performing at a pre-processing circuit:
receiving a first set of data frames from a sensor chip including a plurality of cells, wherein each cell of the plurality of cells is configured to generate detection signals for determining a state of the cell over time, wherein the detection signals are electric signals generated by applying an electric field across a nanopore of a cell of the plurality of cells, wherein the detection signals include data points measured in one or more cycles of an AC signal, each cycle including a first period and a second period, a polarity of the electric field being opposite between the first and second periods, wherein the detection signals include one or more data points in the first period of each of the one or more cycles and one or more data points in the second period of each of the one or more cycles, and wherein each data frame includes the detection signals from the plurality of cells and corresponds to a different time;
extracting information from the detection signals of the plurality of cells in the first set of data frames to obtain first digested information, the first digested information for use in determining the states of the plurality of cells;
generating a first group of one or more digested frames that includes the first digested information extracted from the first set of data frames, wherein a number of digested frames in the first group of one or more digested frames is less than a number of data frames in the first set of data frames; and
sending the first group of one or more digested frames to a processor for use in determining the states of the plurality of cells.

2. The method of claim 1, wherein the first group of one or more digested frames includes one or more data frames from the first set of data frames.

3. The method of claim 1, wherein the state of a cell is selected from:
an open state or a short state of the cell;
a presence or absence of a bilayer in the cell;
a presence or absence of a nanopore in the cell;
a base associated with the cell; or
any combination thereof.

4. The method of claim 1, wherein the first set of data frames includes data frames from the sensor chip that are generated during a formation of the plurality of cells.

5. The method of claim 1, wherein the first set of data frames includes data frames from the sensor chip that are generated during a calibration of the plurality of cells.

6. The method of claim 1, wherein the first set of data frames includes data frames from the sensor chip that are generated in a sequencing cycle.

7. The method of claim 1, wherein the first set of data frames includes data frames from the sensor chip that are generated in multiple sequencing cycles.

8. The method of claim 1, further comprising:
generating a frame map that identifies characteristics of the first group of one or more digested frames.

9. The method of claim 8, wherein the frame map identifies digested frames generated for a sequencing cycle.

10. The method of claim 8, wherein the frame map identifies digested frames generated for multiple sequencing cycles.

11. The method of claim 1, further comprising:
receiving a request to generate a second group of one or more digested frames using a second set of data frames from the sensor chip;
extracting, based on the request, information from the detection signals of the plurality of cells in the second set of data frames to obtain second digested information, the second digested information for use in determining the states of the plurality of cells;
generating the second group of one or more digested frames that includes the second digested information extracted from the second set of data frames; and
sending the second group of one or more digested frames to the processor.

12. The method of claim 11, wherein a number of digested frames in the second group of one or more digested frames is larger than the number of digested frames in the first group of one or more digested frames.

13. The method of claim 11, wherein a number of digested frames in the second group of one or more digested frames is less than the number of digested frames in the first group of one or more digested frames.

14. The method of claim 11, wherein the request identifies a desired digested frame.

15. The method of claim 11, wherein the request identifies a frame map that identifies one or more desired digested frames.

16. The method of claim 1, wherein:
the first period corresponds to a bright period and the second period corresponds to a dark period; and
each of the first group of one or more digested frames includes, for each of the plurality of cells:
a difference between a first data point in the bright period of a cycle and a first data point in the dark period of the cycle;
a difference between a last data point in the bright period of a cycle and the last data point in the dark period of the cycle;
a difference between the last data point in the bright period and the first data point in a next dark period;
a difference between the last data point in the dark period and the first data point in a next bright period; or
a difference between two data points in the dark period of a cycle.

17. The method of claim 1, wherein the one or more digested frames are generated based on at least one of: a difference between the one or more data points in the first period of a cycle, a difference between the one or more data points in the second period of a cycle, or a difference between a first data point of the one or more data points in the first period of a first cycle and a second data point of the one or more data points in the second period of the first cycle or of a second cycle.

18. The method of claim 1, wherein the one or more digested frames are generated based on at least one of: an average or a median of the one or more data points in the first period of each of the one or more cycles, or an average or a median of the one or more data points in the second period of each of the one or more cycles.

19. The method of claim 1, wherein the one or more digested frames are generated based on a data frame of the first set of data frames, the data frame being selected based on determining that a difference among the first set of data frames is below a threshold.

20. The method of claim 1, wherein the one or more digested frames are generated based on a difference between two consecutive data frames of the first set of data frames.

21. The method of claim 1, wherein the pre-processing circuit is part of an integrated circuit that is separate from the sensor chip and from the processor.

22. A device for processing output data from a sensor chip, the device comprising:
a pre-processing circuit; and
a memory coupled to the pre-processing circuit, wherein the pre-processing circuit is configured to:
receive a first set of data frames from the sensor chip, the sensor chip including a plurality of cells, wherein each cell of the plurality of cells is configured to generate detection signals for determining a state of the cell over time, wherein the detection signals are electric signals generated by applying an electric field across a nanopore of a cell of the plurality of cells, wherein the detection signals include data points measured in one or more cycles of an AC signal, each cycle including a first period and a second period, a polarity of the electric field being opposite between the first and second periods, wherein the detection signals include one or more data points in the first period of each of the one or more cycles and one or more data points in the second period of each of the one or more cycles, and wherein each data frame includes the detection signals from the plurality of cells and corresponds to a different time;
store at least some of the first set of data frames in the memory;
extract information from the detection signals of the plurality of cells in the first set of data frames to obtain first digested information, the first digested information for determining the states of the plurality of cells;
generate a first group of one or more digested frames that includes the first digested information extracted from the first set of data frames, wherein a number of digested frames in the first group of one or more digested frames is less than a number of data frames in the first set of data frames; and
send the first group of one or more digested frames to a processor for use in determining the states of the plurality of cells.

23. The device of claim 22, wherein the pre-processing circuit includes a field-programmable gate array (FPGA), a system-on-chip (SoC), an application specific integrated circuit (ASIC), a programmable array logic (PAL), or a complex programmable logic device (CPLD).

24. The device of claim 22, wherein the pre-processing circuit is further configured to:
generate a frame map that identifies characteristics of the first group of one or more digested frames.

25. The device of claim 22, wherein the state of a cell is selected from:
an open state or a short state of the cell;
a presence or absence of a bilayer in the cell;
a presence or absence of a nanopore in the cell;
a base associated with the cell; or
any combination thereof.

26. The device of claim 22, wherein:
the first set of data frames includes data frames from the sensor chip that are generated during a formation of the plurality of cells or during one or more sequencing cycles.

27. The device of claim 22, wherein:
the first period corresponds to a bright period and the second period corresponds to a dark period; and
each of the first group of one or more digested frames includes, for each of the plurality of cells:
a difference between a first data point in the bright period of a cycle and a first data point in the dark period of the cycle;
a difference between a last data point in the bright period of a cycle and the last data point in the dark period of the cycle;
a difference between the last data point in the bright period and the first data point in a next dark period;
a difference between the last data point in the dark period and the first data point in a next bright period; or
a difference between two data points in the dark period of a cycle.

28. The method of claim 1, wherein the detection signals are generated by measuring a resistance of the cell.

29. A method of operating a sequencing system configured to sequence at least 100,000 DNA molecules in parallel, the method comprising performing at a pre-processing circuit:
receiving a first set of data frames from a sensor chip including a plurality of cells, wherein each cell of the plurality of cells is configured to generate detection signals for determining a state of the cell over time, and wherein each data frame includes the detection signals from the plurality of cells and corresponds to a different time;
extracting information from the detection signals of the plurality of cells in the first set of data frames to obtain first digested information, the first digested information for use in determining the states of the plurality of cells;
generating a first group of one or more digested frames that includes the first digested information extracted from the first set of data frames, wherein a number of digested frames in the first group of one or more digested frames is less than a number of data frames in the first set of data frames, wherein the one or more digested frames are generated based on a data frame of the first set of data frames, the data frame being selected based on determining that a difference among the first set of data frames is below a threshold; and
sending the first group of one or more digested frames to a processor for use in determining the states of the plurality of cells.

30. A method of operating a sequencing system configured to sequence at least 100,000 DNA molecules in parallel, the method comprising performing at a pre-processing circuit:
  receiving a first set of data frames from a sensor chip including a plurality of cells, wherein each cell of the plurality of cells is configured to generate detection signals for determining a state of the cell over time, and wherein each data frame includes the detection signals from the plurality of cells and corresponds to a different time;
  extracting information from the detection signals of the plurality of cells in the first set of data frames to obtain first digested information, the first digested information for use in determining the states of the plurality of cells;
  generating a first group of one or more digested frames that includes the first digested information extracted from the first set of data frames, wherein a number of digested frames in the first group of one or more digested frames is less than a number of data frames in the first set of data frames, wherein the one or more digested frames are generated based on a difference between two consecutive data frames of the first set of data frames; and
  sending the first group of one or more digested frames to a processor for use in determining the states of the plurality of cells.

\* \* \* \* \*